(12) United States Patent
Shachar et al.

(10) Patent No.: US 11,020,741 B2
(45) Date of Patent: Jun. 1, 2021

(54) FIELD PORTABLE, HANDHELD, RECIRCULATING SURFACE ACOUSTIC WAVE AND METHOD FOR OPERATING THE SAME

(71) Applicant: Sensor Kinesis Corporation, Los Angeles, CA (US)

(72) Inventors: Yehoshua Shachar, Santa Monica, CA (US); Roger Kornberg, Atherton, CA (US)

(73) Assignee: Autonomous Medical Devices Inc., Santa Monica, CA (US)

( * ) Notice: Subject to any disclaimer, the term of this patent is extended or adjusted under 35 U.S.C. 154(b) by 241 days.

(21) Appl. No.: 16/214,454

(22) Filed: Dec. 10, 2018

(65) Prior Publication Data

US 2019/0176149 A1    Jun. 13, 2019

Related U.S. Application Data

(60) Provisional application No. 62/597,202, filed on Dec. 11, 2017.

(51) Int. Cl.
*B01L 3/00* (2006.01)
*G01N 33/543* (2006.01)
(Continued)

(52) U.S. Cl.
CPC ...... *B01L 3/502715* (2013.01); *G01N 29/022* (2013.01); *G01N 29/222* (2013.01);
(Continued)

(58) Field of Classification Search
CPC .. B01L 3/502715; B01L 3/5027; B01L 3/502; B01L 3/50; G01N 29/022; G01N 29/02; G01N 29/00
(Continued)

(56) References Cited

U.S. PATENT DOCUMENTS 8,436,509 B1    5/2013  Branch
8,548,828 B1   10/2013  Longmire
(Continued)

FOREIGN PATENT DOCUMENTS

WO    WO2014/008434 A2    1/2014
WO    WO2017/173434 A1   10/2017
(Continued)

OTHER PUBLICATIONS

Curtis D. Chin, et.al., "Mobile Device for Disease Diagnosis and Data Tracking in Resource-Limited Settings" Clinical Chemistry 59:4, 629-640 (2013).
(Continued)

*Primary Examiner* — Christine T Mui
(74) *Attorney, Agent, or Firm* — Marcus C. Dawes; Daniel L. Dawes

(57) ABSTRACT

A system and method for performing a portable, fast, field assay of a small sample biological analyte includes a microfluidic cartridge and a reader with which the microfluidic cartridge is selectively communicated. A closed microfluidic circuit mixes and recirculates the analyte with a buffer. A shear horizontal surface acoustic wave (SAW) detector communicates with the microfluidic circuit and has a plurality of channels including at least one functionalized sensing channel in which the mixed analyte and buffer is recirculated and sensed. Capture of the analyte is amplified by recirculation of the analyte and buffer, and detection is amplified by use of an all-purpose endospore display mass amplification.

16 Claims, 16 Drawing Sheets

(51) Int. Cl.
*G01N 29/02* (2006.01)
*G01N 29/22* (2006.01)

(52) U.S. Cl.
CPC .. *G01N 33/54373* (2013.01); *B01L 2200/027* (2013.01); *B01L 2200/04* (2013.01); *B01L 2200/18* (2013.01); *B01L 2300/025* (2013.01); *B01L 2300/0627* (2013.01); *B01L 2300/0816* (2013.01); *B01L 2300/0887* (2013.01); *B01L 2400/0436* (2013.01); *B01L 2400/0475* (2013.01); *B01L 2400/0605* (2013.01); *G01N 2291/022* (2013.01); *G01N 2291/0255* (2013.01); *G01N 2291/0256* (2013.01)

(58) Field of Classification Search
USPC .......................................... 422/502, 500, 50
See application file for complete search history.

(56) References Cited

U.S. PATENT DOCUMENTS

2006/0205061 A1* 9/2006 Roukes ............ G01N 33/54366
435/287.2
2011/0223583 A1 9/2011 Gordon
2012/0329142 A1 12/2012 Battrell
2016/0132632 A1 5/2016 Zavoronkovs et al.
2016/0238553 A1 8/2016 Shachar

FOREIGN PATENT DOCUMENTS

WO WO2018/057201 A1 * 3/2018 ............. G01N 29/00
WO WO 2018/213254 A1 * 11/2018 ............. G01N 29/02

OTHER PUBLICATIONS

Alex Nemiroski et.al., "Universal mobile electrochemical detector designed for use in resource-limited applications" 11984-11989, PNAS, Aug. 19, 2014, vol. 111, No. 33.
David O. Soti et.al., "Feasibility of an innovative electronic mobile system to assist health workers . . . " Soti et al. Malar J (2015) 14:430 DOI 10.1186/s12936-015-0965-z.
Hojeong Yu et.al. "Mobile Platform for Multiplexed Detection and Differentiation of Disease-Specific Nucleic Acid Sequences . . . " Anal. Chem. 2017, 89, 11219-11226.

* cited by examiner

FIELD PORTABLE, HANDHELD, RECIRCULATING SURFACE ACOUSTIC WAVE AND METHOD FOR OPERATING THE SAME

RELATED APPLICATIONS

The present application is related to U.S. Provisional Application Ser. No. 62/597,202, filed on Dec. 11, 2017, which is incorporated herein by reference and to which priority is claimed pursuant to 35 USC 119.

BACKGROUND

Field of the Technology

The invention relates to the field of biosensing employing a microfluidic circuit for supplying analyte to a surface acoustic wave sensor (SAW), wherein the principle of operation is based on rapid association of a biological species onto functionalized sensor. More particularly, the invention is directed to convection enhanced delivery (CED) as a means to reduce the diffusive timescales, thereby improving the probability of the analyte encountering the antibodies present on the sensor lane. The use of a microfluidic circuit enables multiple biological sequencing events whereby analyte conjugation, bio-amplification, and detergent administration reduces false positives of the measured result. Further, use of biochemical amplification reduces the limit of detection (LOD) to a measurable value between femtogram(s) (fg) to pictogram(s) (pg) per milliliter (ml) of volume.

Description of the Prior Art

The prior art for the subject matter generally defined under the heading of "how to reduce the limit of detection for identifying a pathogen, be it a protein, DNA, RNA, or viruses" is related to the ability of the apparatus and its biochemical probe to respond to a minimal limit of detection (LOD) based on concentration with values ranging from femtogram to picogram of an analyte with a volume of milliliter of liquid. The minimal LOD at such concentration can be operationally defined by the two fundamental concepts of "capture" and "detection" and in turn relates to the measure of the apparatus in question to address the resolution of the measuring system to address such low concentration of the LOD by providing clear metrics defining the relationship between the minimum mass conjugated on the surface of the sensor versus the equivalent electrical change registered by the measuring device. The challenge of LOD versus resolution of the measured output is the central issue the current invention is concerned with.

The unique challenges posed by a minimal LOD and the solution provided by the current invention is further complicated using a sensing modality associated with the use of a sheer horizontal surface acoustic wave biosensor approach which fundamentally relies on the ability of the sensor and its electronic reader to resolve mass accumulation over the sensing lane(s) on the order of femtograms to picograms per $ml^{-1}$.

There is a continuing need to be able to analyze very small samples of DNA-based analytes in the field within short time periods by untrained personnel using low cost handheld devices. However, no such devices currently exist.

Analysis of DNA-based analytes collected in patients or in the field has been typically performed by utilizing biochemical amplification of the analyte, such as by the polymerase chain reaction (PCR), to increase the amount of analyte until it reaches a magnitude at which clinical or laboratory DNA analysis can reliably be made. The vast majority of PCR methods rely on thermal cycling, which involves exposing the reactants to cycles of repeated heating and cooling, permitting different temperature-dependent reactions, specifically, DNA melting and enzyme-driven DNA replication, to quickly repeat many times in sequence. Primers (short DNA fragments) containing sequences complementary to the target region, along with a DNA polymerase, after which the method is named, enable selective and repeated amplification. As PCR progresses, the DNA generated is itself used as a template for replication, setting in motion a chain reaction in which the original DNA template is exponentially amplified. PCR is thus a carefully controlled and time-consuming laboratory-intensive methodology, which cannot realistically be practiced in a short period of time in the field with a low-cost handheld device by untrained personnel.

Another prior technology for analyzing small samples of DNA-based analytes is the use of analyzers that rely on diffusion of the analyte in a functionalized sensor, such as an enzyme-linked immunosorbent assay (ELISA). As an analytic biochemistry assay, ELISA involves detection of an analyte in a liquid sample by a method that continues to use liquid reagents during a controlled sequence of biochemical reactions that generate a signal, which can be easily quantified and interpreted as a measure of the amount of analyte in the sample. The sample stays liquid and remains inside a reaction chamber or well needed to keep the reactants contained, as opposed to a "dry lab" test that use dry strips. Even if the sample is liquid (e.g. a measured small drop), the final detection step in dry analysis involves reading of a dried strip by methods such as reflectometry and does not use a reaction containment chamber to prevent spillover or mixing between samples.

As a heterogenous assay, ELISA separates some components of the analytical reaction mixture by adsorbing certain components onto a solid phase which is physically immobilized. In ELISA, a liquid sample is added onto a stationary solid phase with special binding properties and is followed by multiple liquid reagents that are sequentially added, incubated, and washed, followed by some optical change, e.g. color development by the product of an enzymatic reaction, in the final liquid in the well from which the quantity of the analyte is measured. The qualitative reading is usually based on detection of intensity of transmitted light by spectrophotometry, which involves quantitation of transmission of some specific wavelength of light through the liquid as well as the transparent bottom of the well in the multiple-well plate format. The sensitivity of detection depends on amplification of the signal during the analytic reactions. Since enzyme reactions are very well-known amplification processes, the signal is generated by enzymes which are linked to the detection reagents in fixed proportions to allow accurate quantification.

The analyte is also called the ligand because it will specifically bind or ligate to a detection reagent, thus ELISA falls under the bigger category of ligand binding assays. The ligand-specific binding reagent is immobilized, i.e., usually coated and dried onto the transparent bottom and sometimes also side wall of a well (the stationary "solid phase"/"solid substrate" here as opposed to solid microparticle/beads that can be washed away), which is usually constructed as a multiple-well plate known as the "ELISA plate." Conventionally, like other forms of immunoassays, the specificity of antigen-antibody type reaction is used because it is easy to raise an antibody specifically against an antigen in bulk as a reagent. Alternatively, if the analyte itself is an antibody, its target antigen can be used as the binding reagent. It can readily be appreciated that ELISA cannot realistically be practiced in a short period of time the field with low cost handheld devices by untrained personnel.

There are several technical constraints that have prevented the successful development of a low cost, field portable handheld device useable by untrained personnel to reliably analyze small DNA-based samples in short time periods, namely or the order of 15 minutes or less. These constraints include the inherent problem and limitation of using any kind of diffusion process in a sensing apparatus to analyze the μL sample. Depending the sensing mechanism employed, the capture fraction of the analyte by the sensor is typically very low, the sample size of the analyte is typically in the tens of microliters or a few small drops of liquid, and the diffusion times can be long, often stretching to many hours with typical prior art technologies.

With small sample sizes, typically 50 μL or less, the amount of mass of DNA-based analyte is in the range of picograms. For example, at least 74% of the mass of *E. Coli* is water so that any sensing process applied to *E. Coli* that depends on the difference in the mass of the DNA-based analyte over the mass of the aqueous solution or buffer in which the analyte is carried and diffuses will need to be able to reliably detect a small fraction of the small sample size.

The sample sizes collected in typical field applications are so small that an amplification process is necessary to reliably measure the presence and amount of the analyte. The analyte must not only be detected, but clearly detected with high repeatability to avoid false positives. Clinical standards require that the detected signal be at least three times larger than the average noise level in the detector, namely a signal-to-noise ratio of more than three.

Finally, for the device to be usable in the field, it must be of such a construction and nature that untrained operators can reliably employ the device and method without inviting the introduction of unintended sampling errors or variations. In prior experiences with laboratory functionalized surface acoustic wave (SAW) detectors, for example, highly variable test results have been obtained due to small variations in the environmental conditions at the time of loading the sample into the SAW detector. The temperature of the laboratory, the operation of a local air conditioning and heating system near the detector, an open nearby window, variations in humidity and other unsuspected environmental conditions at the time of sample loading can change the result the detector records.

These and other constraints are substantial, cannot be avoided, and must be overcome in order to be able to analyze very small samples of DNA-based analytes in the field within short time periods by untrained personnel using low cost handheld devices. What is needed therefore is an apparatus and a series of inventive steps which can be employed to address this challenge and operationalize the contributing factors which relate to capture and detection.

SUMMARY OF THE INVENTION

The detection limit is of great importance in biomolecular assay and sensor development. There has been an increasing pressure to push the detection limit of bioanalytical techniques to lower levels while increasing resolution. This pressure is largely driven by a demand for new molecular diagnostic tests for early stage cancer detection and diagnosis. At early stages of cancer development, the amount of cancer biomarker molecules released from the tumor to the blood or other biological fluids is very small. Naturally, one assumes that a more sensitive analytical technique that can "catch" these cancer biomarkers at lower concentrations the earlier will cancer be detected. Under this general premise, pursuing lower level detection limits has become a major goal of bioanalytical technology development and this effort is the focus of the current invention where the use of biomass with specificity to the analyte in question is being promoted under the general guidelines of employing endospores with genetically modified expression to respond to the analyte, thereby increasing its detectable mass proportional to the bound analyte to its antibody in the forms of a customary titled ELISA sandwich.

It is not uncommon to see detection limits in the fg-pg $ml^{-1}$ range for protein antigens, and sometimes even down to the single molecule level. While pursuing bioanalytical techniques and products with higher sensitivities and lower detection limits, it's important to ask a critical question: is the claimed/expected detection limit theoretically achievable? If by theory, an analytical method cannot possibly achieve the sensitivity as claimed, attempted use of such methods for expected high sensitivity analysis can only lead to a waste of research effort and resources, and sometimes, misleading results. This issue of limited available biological species defined by its concentration (within the aqueous volume) and the ability of the detector to sense such limited presence of the antigen is determined by the test apparatus resolution. These and other considerations which limit our ability to measure concentration of biological species in the order of fg-pg $mL^{-1}$, and is the focus of the current invention.

Detecting biochemical species with LOD ranging from femtogram to picogram value is mandated by the need for early detection of biological species (biomarkers present in blood, saliva, urine or other bodily fluids), where such species are invariably marked by their low concentration value. The aim of this entire exercise is to achieve a reliable measurement of a biological capture between an antibody and its antigen.

The use of a microfluidic chamber with attributes which enable the use of sequencing of chemical and biological events should be viewed within the context of the prior art such as noted by "High-Frequency Shear-Horizontal Surface Acoustic Wave Sensor" U.S. Pat. No. 8,436,509 May 7, 2013, and "Carbon Nanotube BioFET with a Local Amplifier in a System Array for Analysis of Biomarkers and Method of Analysis of Same", U.S. patent application Ser. No. 12/581,758 filed Oct. 19, 2009, hereby incorporated by reference in their entirety. These detection technologies are enabled by the use of the microfluidic apparatus as described below.

As additional reference for use of bio-amplification whereby mass is added to the analyte in a sequence described by the specification noted below is further supported by the publication of the technique noted by Brenner S, Lerner RA (June 1992) entitled "Encoded combinatorial chemistry," Proc. Natl. Acad. Sci. U.S.A. 89 (12): 5381-3, and where such technique is a foundational disclosure relevant to the biochemical enhancement utilized in the illustrated embodiments.

As shall be described in further detail below, this effort is set relative to the use of a biosensor with the attributes noted by employing a shear horizontal surface acoustic wave biosensor (SH-SAW) where mass accumulation associated with any biological species and its conjugate analyte increases the mass loading which thereby provides an electrical signal proportional to the attenuation of the waveform and relative to its mass accumulation over the sensor lane.

Through prior experimentation, it has been discovered that the limit of detection (LOD) of the SH-SAW sensors is dictated by the frequency band utilized and corresponds roughly to the order of one picogram (the resolution of the measuring device). This arises from the frequency used (325 MHz) such that resolution is maximized and where elastic energy does not escape the lane, thereby increasing the insertion losses (IL) of the apparatus. For a measurement to be deemed statistically significant by the National Institute of Standards and Technology (NIST), a signal value must be three times larger than the signal to noise ratio (SNR). The LOD therefore arises from this relationship set forth by NIST, and with the use of the operational frequency (325 MHz) the apparatus output measured in phase ($\phi$) of the frequency will obey the formalism noted by the equation for the LOD expressed as $$LOD = \frac{3 \times N_f}{S_\sigma^\phi \times \phi_0} \Delta \sigma_r = \frac{3 \times N_f}{S_\sigma^\phi \times \phi_0}.$$

Using this formalism, coupled with our experimental frequency of 325 MHz, we obtained the resulting minimum LOD of approximately one picogram of mass coupled with bio-amplification using the microfluidic device described below as illustrated in the Figures.

In this application, we describe a procedure whereby the use of a bio-amplification method of specifically conjugating a single endospore to the analyte in question contributes an additional 1 pg of mass to the analyte in a form resembling an ELISA sandwich, thereby providing a means by which such mass loading can achieve the required detection limits.

With the assumption that the analyte concentration is set at level of femtogram to picogram in a milliliter volume (fg-pg ml$^{-1}$), and further due to the apparatus limitation of a resolution of 1 picogram, a need to create a mass amplification step is apparent to ensure detection of target antigens at concentrations that are within the necessary limits deemed significant.

An additional limitation of performing a bioconjugation of analyte to its antibody is the fact that the limit of detection mandates a bio-amplification step. This requirement of enhancing the analyte mass to overcome the apparatus resolution (1 pg threshold mass of detection) is further complicated by the fact that the amplification steps employing endospores, polymer structures with a suitable mass, and/or magnetic beads necessitate the removal of nonspecific elements, such as sedimented debris and gravitationally bound masses, which must be removed to avoid false positive readings. To that extent, the current invention employs a technique of convection enhanced delivery in a microfluidic chamber.

As shall be demonstrated by the illustrated embodiments, the use of a microfluidic chamber with an active convection enhanced delivery (CED) enables sequencing within the chemical reaction necessary in establishing the LOD at the levels noted above.

Endospores are genetically modified bacteriophage that have been engineered to express specific single-chain variable fragments (scFv), which are antibody-like proteins on the surface at the tips of the phage. These endospores are designed to have a high affinity for binding to a particular analyte, while possessing an expressed mass of one picogram, a detectable unit of mass for the SAW sensor. Additionally, endospores possess a vectoral affinity and rigidity that works to support the strategy of mass amplification in a surface acoustic wave sensing modality. By employing endospores as a bioamplifier, a three-piece ELISA "sandwich" is created, consisting of 1) an antibody capture site welded to the sensor, 2) a target antigen captured from the fluid sample, and 3) an endospore that is introduced after initial antibody-antigen association has occurred. Because a single endospore has a mass thousands of times greater than the target antigen, this ELISA sandwich binding process allows us to detect target materials that would otherwise be undeletable because of the LOD of the device. Before final measurements of the solid-state phase shift are recorded, a detergent is added to remove any sedimented endospores not electrochemically bound to the sensor to prevent any mass contributions that would return a false positive.

This process of attaching the endospore to the analyte can be done in two ways. A pre-mixing of analyte and endospore can occur where both are introduced in a mixing chamber before being sent to the SAW sensor for capture. This would lead to a markedly diminished signal resulting from the fact that many analytes would be absorbed onto a single spore, in addition to the low rotational and translational diffusion rates of a spore, leading to an order of magnitude lower rate of analyte binding to the chip. Another problem with this method is that a deviation from the linear relationship between the capture-to-concentration rate is apparent, as the change in mass would no longer correspond to a 1:1 ratio of analyte concentration, as free-floating analytes can be captured by the endospores before they can interact with the chip.

The second option is to have two additional chambers, one for spores to be introduced following analyte recirculation over the chip, and a second to introduce a detergent to wash away unbound spores. To further enhance the signal-to-noise ratio and establish a quantitative measurement, the cartridges disclosed below utilize the multi-reservoir system of sequentially delivering biological mass amplifiers and detergent separately from the initial analyte sample, reducing nonspecific binding of endospores which would either generate nonlinear ratios of analyte to endospore, thus making measurements qualitative, or generate false positive measurements.

The addition of mass loading to the SAW sensor during shear wave propagation enables a detectable phase shift in the acoustic waveform to be observed, because of the attenuation of the surface shear waves in response to the additional mass. This correlates directly to the ratio of analyte surface coverage of the SAW sensor at equilibrium to total available surface sites, as will be explained below. This final solid-state phase shift is registered electronically by the reader mechanism, which uses a microprocessor to analyze the data and to store or transmit the results to the user, be it a physician or institution.

Given an antibody-antigen reaction that follows an adsorption pattern according to the Langmuir Isotherm, the surface adsorption process is expressed as:

[Antibody]+[Analyte]⇔[Antibody–Analyte complex], or

[Ab]+[S]⇔[AbS]

With forward reaction constant $k_{on}$ and reverse reaction constant $k_{off}$. The adsorption can be described using the differential equation:

$$\frac{d\Gamma}{dt} = D\left(\frac{\partial C}{\partial x}\right);$$

where $D \equiv$ Diffusion Constant $\left(\frac{cm^2}{s}\right)$, where $\Gamma \equiv$ Surface coverage $\left(\frac{molecules}{cm^2}\right)$, The Equilibrium constant:

$$K \equiv \frac{k_{on}}{k_{off}} = \frac{\Gamma}{(\Gamma_{max} - \Gamma)C_b}; \Gamma_{equilibrium} = \Gamma_{max}KC_b,$$

where $\Gamma_{max}$ is the total number of available antibody binding sites on the surface of the detector. The kinetics can be related to the rate of diffusion in the solution by $$J_D = \text{Rate of diffusion} = \frac{D(C_b - C_s)}{L},$$

where L is the diffusion length and the simple Langmuir first-order rate of adsorption (for low coverage) at the surface, $$J_R: J_R = k_{ads}C_s(\Gamma_{max} - \Gamma).$$

When using the SAW biosensor, the endpoint is typically used, i.e. when the system reaches an apparent steady-state (the delta phase value levels off). At steady-state (S.S.)

$$J_D = J_R \therefore \frac{D(C_b - C_s)}{L} = k_{ads}C_s(\Gamma_{max} - \Gamma).$$

Solving for the surface concentration at S.S.

$$C_S = \frac{C_b}{1 + \frac{k_{ads}L(\Gamma_{max} - \Gamma)}{D}}, \text{ or } C_S = \frac{C_b}{1 + \theta},$$

where $\theta$ is known as the Thiele modulus, a dimensionless parameter. For cases where the value of $\theta \gg 1$, $C_s$ approaches 0, and any antigen contacting the surface will be absorbed onto it. In this case, the rate of surface coverage is determined by the rate of diffusion in solution or $$J_D = \frac{D(C_b - C_S)}{L}.$$

For cases where $\theta \ll 1$; $C_s$ approaches $C_b$. Therefore, the diffusion in the solution is faster than the adsorption and the kinetics of the process is governed by the rate of adsorption at the surface. In this case:

$$J_R = k_{ads}L(\Gamma_m - \Gamma)$$

when not in a limiting case, the equation for Cs is solved. Based on literature values, the value of $\theta$ is calculated to be $2 \times 10^{-9}$; $\theta \ll 1$. Assuming a diffusion constant given by the Stokes-Einstein equation gives $$D = \frac{k_b T}{6\pi \eta r} \cong 5 \times 10^{-7}.$$

The packing density of the antibodies nanoparticles in the immunoassay assay is estimated at $$10^{10} \frac{molecules}{cm^2}.$$

Therefore, the rate of change of the surface coverage can be given by an adsorbing species is given by the simplified equation:

$$\frac{d\Gamma}{dt} k_{ads}C_b(\Gamma_{max} - \Gamma).$$

Since all experiments are performed at approximately the same temperature (temperature controlled setup), assume that $k_{ads}$ remains constant. Integrating with initial conditions $\Gamma(0)=0$; $\Gamma(t)=\Gamma$, the solution becomes:

$$\Gamma = \Gamma_{max}(1 - e^{k_{ads}c_b t}), \text{ or } \frac{\Gamma}{\Gamma_{max}} = 1 - e^{k_{ads}c_b t}.$$

The time constant which determines the relaxation time for each run, $\tau$, is given as $$\tau = \frac{1}{k_{ads}c_b}.$$

The $$\frac{\Gamma}{\Gamma_{max}}$$

is directly proportional to the corrected, normalized phase change. Therefore, the correlated values $$\frac{\Gamma}{\Gamma_{max}} = \frac{\text{delta phase (sample)}}{\text{delta phase standard (glycerol)}} = 1 - e^{\left(-\frac{t}{\tau}\right)}.$$

The signal is assumed to reach saturation at the end of $3\tau$, which corresponds to 95% of the delta phase value. This is estimated to be less than 10 minutes. The delta phase values depend on both the concentration of the antigen and the incubation time. The transient is assumed to typically last less than 10 minutes but is dependent and the antigen antibody combination.

There are two fundamental problems associated when measuring small concentrations of antigen of biological species, where conjugation rate (K+) between antibody and its counterpart (such as: DNA or DNA fragment, RNA, protein, bacteria, or virus) are determined by an association constant antibody. The factors which the application of convection enhanced diffusion solves is the ability of the apparatus to reduce the effect of the diffusion coefficient limitation as well as the association rate of a small sample of antigen to provide a measurable and consistent value of the biological assay in question. By incorporating convection and diffusion techniques to homogenize antigen concentration throughout the microfluidic apparatus, spontaneous electrochemical capture of proximal antigens to the antigen surface occurs more frequently than by diffusion alone, reducing timescales for the apparatus to saturate from 6 hours in absence of CED to approximately 10 minutes with CED.

For mass transport of a dissolved species (analyte), concentration gradients will drive the transport mechanism diffusion. Specially fabricated scFv antibody capture sites are designed to have high association rates, so any analyte that passes within one micrometer of the SAW antibody capture plate is assumed to covalently attach to the chip. Where there is fluid motion, sites of active and passive mixing can be used to reset the vertical concentration gradient and homogenize the species normal to the chip within the channel. Because of the closed-circuit nature of the microfluidic apparatus, mixing sites implemented in parallel before the SAW sensor will act by convection to maintain a species concentration in the capture range of one micrometer above the channel and deposit this mixed solution onto the antibody capture sites. Mixing will also remove any negative concentration gradient in the horizontal downward direction that has accumulated in the fluid to maximize the chance of antibodies being present in the capture radius without the need to wait for diffusion timescales to homogenize the fluid and saturate the associative layers. The expression for the combined convection diffusion equation is:

$$\frac{\partial c}{\partial t} = \underbrace{\nabla \cdot (D \nabla c)}_{1} - \underbrace{\nabla \cdot (\vec{v} c)}_{2} + \underbrace{R}_{3},$$

where the first term describes diffusion, the second term describes convection, and the third term describes removal of the species onto the sensor via association. This relationship is utilized in a technique known as convection enhanced delivery, or CED. During CED, convection and diffusion occur simultaneously to increase the probability of capture between an antibody layer and a suspended antigen solution. CED works to deposit material into the electrochemical binding range through convection at a sufficiently high rate such that the convection term acts as a dominant factor, while reducing the effect of the diffusion coefficient limitation in the relationship. Because of the constant homogenization of analytes through convective fluid motion, the contribution of diffusion in replacing the captured analytes becomes almost negligible over the timescale in which a concentration gradient can be established due to association onto the sensor and before the fluid passes over the entirety of the SAW association site before being returned to the recirculating microfluidic network.

To fully integrate convection enhanced delivery into the mass transport of analytes, the fluid motion and its behavior will have to be derived for this application. The Navier-Stokes Equations are a set of conservation equations that dictate the behavior of fluid motion. By simultaneously solving both for conservation of momentum and mass, the behavior of the fluid flow can be obtained. For a Newtonian fluid, the momentum conservation is expressed as $$\underbrace{\rho\left(\frac{\partial u}{\partial t} + u \cdot \nabla u\right)}_{1} = \underbrace{-\nabla p}_{2} + \underbrace{\nabla \cdot \left(\mu(\nabla u + (\nabla u)^T) - \frac{2}{3}\mu(\nabla \cdot u)I\right)}_{3} + \underbrace{F}_{4},$$

while the conservation of mass is expressed as $$\frac{\partial \rho}{\partial t} + \nabla \cdot (\rho u) = 0.$$

For the momentum equation, the terms represent (1) inertial forces, (2) pressure forces, (3) viscous forces, and (4) external forces. For application in microfluidic flow modeling, a second principle must be introduced to reduce the equation so that it can numerically be computed and utilized in the design stage of development. The Reynolds number is a dimensionless number that expresses the ratio of 1) inertial forces to 3) viscous forces. It can be calculated from the equation $$\mathrm{Re} = \frac{\rho u L}{\mu},$$

where ρ is me fluid density $$\left(\frac{\mathrm{kg}}{\mathrm{m}^3}\right),$$

u is the fluid velocity $$\left(\frac{\mathrm{m}}{\mathrm{s}}\right),$$

L is the characteristic linear dimension of the application (m), and μ is the dynamic viscosity (Pa·s). For Re<1, viscous forces dominate, and the flow is laminar. For this application, the computed Re is Re<1. Therefore, for the Navier-Stoke fluid transport equation for this application, the inertial term (1) and external forces (4) are neglected. Additionally, the incompressible nature of the fluid at application velocities means that the velocity gradient term is also neglected. The combined Navier-Stoke equation for laminar regime therefore reduces to $$0 = \underbrace{-\nabla p}_{2} + \underbrace{\nabla \cdot (\mu(\nabla u + (\nabla u)^T))}_{3} \text{ and}$$

$$\frac{\partial \rho}{\partial t} + \nabla \cdot (\rho u) = 0.$$

This system of equations, coupled with the boundary conditions arising from the geometry of the apparatus, is used to numerically solve for both a pressure and velocity field within the microfluidic circuit. Because the flow is laminar, there is no inertial mixing occurring normal to the velocity gradient, and any circulation of material would eventually result in a uniform concentration gradient thorough the circulation path and would result in the elimination of any decrease in saturation time resulting from convection and a return to diffusive timescales for saturation. This problem is addressed by the introduction of both an active piezo mixing apparatus and passive mixing channel component in the microfluidic schematic to homogenize the sample fluid with every pass before it is administered onto the surface acoustic wave (SAW) sensor. Additionally, within the timescale of our application, the fluid circulates approximately 50 times thorough the circuit. As a result, during any of the 50 loops, any analytes that pass within 1 µm of the chip are associated onto the surface. This perpetual looping combined with mixing results in an increase in the statistical odds of the analyte samples being encountered by the antibodies. Because of this, the diffusion coefficient term (1) of the convection diffusion equation at the removal site R can be neglected, as the scales in which convection are able to deliver analytes are much faster than diffusion, so that diffusion becomes negligible.

There exists a tool to be utilized in quantifying the effects of mass transport through convection and diffusion. The Péclet number (Pe), is a dimensionless number which expresses the ratio of contributions of mass transport via convection and diffusion:

$$Pe = \frac{N_{conv}}{N_{diff}} = \frac{c_i |u|}{D \nabla c_i} = \frac{LU}{D}.$$

Similar to how the Reynolds number describes contributions to momentum transport, the Péclet number expresses contributions to mass transport across a characteristic length scale L. The Péclet number is solved for our geometry with Re<1 and is also found to be <1. Because the Péclet number is less than one, the mass will primarily be transported via diffusion from the fluid onto the chip at the length scale of analyte-antibody interaction. This is incorporated into the greater CED flow model by a virtual increase in the diffusion coefficient (or an increase in the effectiveness of diffusion) through homogenization before the fluid reaches the sensor via a passive mixing site in the microfluidic system. By decreasing the characteristic length scale of diffusion even further in these mixing sites, an increased concentration gradient arises which leads to the occurrence of mixing by diffusion, but at greatly reduced timescales. Although the antigens are deposited via diffusion onto the chip, the convective mixing helps to replenish the lower layers by mechanical homogenization and prevents a concentration gradient from developing that would impede sensor saturation timescales. Because of the electrochemical attraction that exists between an antibody and antigen, there exists a range in the fluid flow for which spontaneous capture is likely to occur. As a result, homogenization allows for quicker sample saturation as with each pass the lower layers are refreshed and need not depend on diffusion timescales to replenish the layers in which capture can occur.

There exists an intrinsic association rate $$K \equiv \frac{k_{on}}{k_{off}}$$

that dictates the capture rate of analytes to the fragmented antibody layer. This property is intrinsic to the covalent reaction between the analyte and its receptor antibody. Although the electronic affinity for capture between a single antibody and its target analyte cannot be altered through biochemical techniques, it can be virtually increased through several geometric applications. One such application is the increase in the total number of available antibody capture sites. By increasing the capture site density on the sensor, a virtual increase is created in the association rate between antibody and analyte, as spontaneous capture is inherently more likely to spontaneously occur as the number of available binding sites increase. Simultaneously, advances in biochemical laboratory techniques allow for the packing density of scFv antibodies onto the stem.

Another method employed for altering the association rate (k+) is generated by the fluid motion. By increasing the volume motion, we alter the natural constants associated with the binding rate between the analyte and antibody as well as the timescales of diffusion coefficient. Although the K constant and the D constant are inherently unchangeable, with the use of CED to refresh concentrations at the fluid surface boundary and prevents a concentration gradient from developing that would hinder association rate because of decreased availability of analyte sample as a function of time and orientation. By maintaining a homogenized analyte concentration, the probability of an analyte passing within one um of the functionalized sensor is greatly increased which results in an increased amount of binding and much shorter timescales for binding, thereby increasing mass loading that the device is capable of detecting.

It can now be understood that the illustrated embodiments of the invention are directed to a system for performing a portable, fast, field assay of a small sample biological analyte. The system includes a microfluidic cartridge; and a reader with which the microfluidic cartridge is selectively communicated.

The current invention provides an apparatus for performing a field assay of an analyte. The apparatus includes a microfluidic cartridge with a closed microfluidic circuit for mixing and recirculating a fluid and a reader with which the microfluidic cartridge selectively communicates. The closed microfluidic circuit principally includes a shear horizontal surface acoustic wave (SAW) detector having a plurality of channels, a first manifold configured to distribute the fluid uniformly to the plurality of channels of the SAW detector connected to a passive mixer, and a second manifold configured to remove the fluid from the plurality of channels of the SAW detector which is connected to a return line. The microfluidic circuit further includes a pump which is configured to repeatedly circulate the fluid in order through the first manifold, the plurality of channels of the SAW detector, the second manifold, and then returned to the first manifold for a predetermined number of cycles over a predetermined time period in order to increase the probability of a reaction occurring within the SAW detector and thereby reducing the time required for the SAW detector to measure the fluid.

In one embodiment, the shear horizontal surface acoustic wave (SAW) detector has at least one channel functionalized with an antibody to provide a sensing channel through which the fluid is recirculated and sensed and a plurality of non-functionalized channels to provide a plurality of reference channels through which the fluid is recirculated.

In another embodiment, the fluid being recirculated is comprised of an analyte and a buffer, a functionalized biological mass amplifier, or a detergent complex.

In another specific embodiment the microfluidic circuit further includes a reservoir chamber comprising a perforating membrane, a bubble trap, and an active mixer fluidly coupled to the reservoir chamber and to the bubble trap. In this embodiment, the active mixer is configured to mix the fluid into a homogenous mixture. Additionally in this embodiment, the return line is fluidly coupled to the second manifold and to the reservoir chamber.

In a related embodiment, the pump disposed within the microfluidic circuit is configured to circulate the analyte through the sensing channel of the SAW detector so that at least one analyte molecule is captured by the antibody disposed within the sensing channel of the SAW detector.

The pump is also configured to circulate a plurality of functionalized biological mass amplifiers contained within the fluid through the sensing channel of the SAW detector so that at least one of the plurality of functionalized biological mass amplifiers interacts with the at least one analyte molecule captured by the antibody so that an enzyme-linked immunosorbent assay (ELISA) chain is created.

Additionally, the pump is further configured to circulate a detergent complex through the sensing channel of the SAW detector so that a plurality of functionalized biological mass amplifiers which are not interacting with the at least one analyte molecule are removed from the sensing channel of the SAW detector to reduce the probability of false positives detected by the SAW detector.

In a separate embodiment, the reader of the apparatus includes a cartridge loader and a motorized cartridge carrier which is removably coupled to the cartridge loader. In this embodiment, the motorized cartridge carrier is configured to accommodate the microfluidic cartridge.

In yet another embodiment, the microfluidic cartridge comprises at least three different chambers, namely at least one chamber containing an analyte and a buffer, at least one chamber containing a functionalized biological mass amplifier, and at least one chamber containing a detergent complex.

The invention further includes a method for performing a field assay of a small volume sample of a fluid. The method includes selectively communicating a microfluidic cartridge with a reader, circulating the fluid through a microfluidic circuit disposed within the microfluidic cartridge, and controlling the operation of the microfluidic cartridge through the reader. The method further includes displaying a result obtained by the microfluidic cartridge on a display of the reader. Circulating the fluid through the microfluidic circuit specifically includes uniformly distributing the fluid through a first manifold to a plurality of channels including at least one functionalized sensing channel disposed within a shear horizontal acoustic wave (SAW) detector and then detecting an analyte disposed within the fluid using the at least one functionalized sensing channel of the SAW detector. Next, the fluid is extracted from the plurality of channels through a second manifold fluidly communicated to a return line and then repeatedly pumped sequentially through the first manifold, the plurality of channels of the SAW detector, the second manifold, and then returned to the first manifold for a predetermined number of cycles over a predetermined time period, thereby increasing the probability of a reaction occurring within the SAW detector and reducing the time required for the SAW detector to measure the fluid.

In one embodiment, circulating the fluid through the microfluidic circuit includes introducing the analyte and a buffer into a reservoir chamber, mixing the analyte and buffer to produce a homogenous mixture by sending the analyte and buffer through an active mixer, and then removing air bubbles from the homogenous mixture using a bubble trap. Next, a uniform flow of the homogenous mixture is provided to the first manifold using a passive mixer fluidly connected to the bubble trap and the first manifold. The homogenous mixture is then pumped to the reservoir chamber through the return line.

In another embodiment, detecting the analyte disposed within the fluid using the at least one functionalized sensing channel of the SAW detector specifically includes repeatedly circulating the analyte through the SAW detector so that at least one analyte molecule is captured by an antibody disposed on a surface of the at least one functionalized sensing channel disposed within the (SAW) detector. In a related embodiment, detecting the analyte disposed within the fluid using the at least one functionalized sensing channel of the SAW detector is accomplished by uniformly distributing a biological mass amplifier to the plurality of channels of the SAW detector so that at least one biological mass amplifier interacts with the at least one analyte molecule captured by the antibody so that an enzyme-linked immunosorbent assay (ELISA) chain is created. Additionally, a detergent complex may be uniformly distributed to the plurality of channels of the SAW detector so that a plurality of biological mass amplifiers which are not interacting with the at least one analyte molecule are removed from the sensing lane of the SAW detector to reduce the probability of false positives detected by the SAW detector.

In another embodiment, circulating the fluid through the microfluidic circuit further includes increasing the kinetics of the fluid and detecting the analyte using the at least one functionalized sensing channel of the SAW detector specifically involves detecting at least 1 picogram of the analyte.

In a further embodiment, the biological mass amplifier which is distributed to the plurality of channels of the SAW detector is a virus, a Ab-Conjugated endospore, or a scFv-conjugated endospore.

In yet another embodiment, the microfluidic cartridge is selectively communicated with the reader by first accommodating the microfluidic cartridge within a cartridge carrier and then inserting the cartridge carrier into a cartridge loader disposed on the reader.

In a separate embodiment, selectively communicating the microfluidic cartridge with the reader further includes providing a motorized loading and unloading of the microfluidic cartridge to and from the cartridge loader.

The invention further provides a method of using a microfluidic cartridge with a portable system for performing a field assay of a small volume sample of a biological analyte. The method includes recirculating the analyte with a buffer within a microfluidic circuit that is disposed within the microfluidic cartridge and then detecting the analyte using a shear horizontal surface acoustic wave (SAW) detector which is communicated with the microfluidic circuit. In this embodiment, the SAW detector has a plurality of channels including at least one functionalized sensing channel in which the mixed analyte and buffer is recirculated and sensed and at least one non-functionalized reference channel in which the mixed analyte and buffer is recirculated. Preferably, recirculating and detecting the analyte and buffer are performed in less than 15 minutes while the kinetics of the analyte and buffer are increased by recirculating the analyte and buffer through a manifold and a propellant mechanism so as to increase the probability of an encounter of the analyte with an antibody disposed within the at least one functionalized sensing lane of the SAW detector. Finally, detecting the analyte using the (SAW) detector communicated with the microfluidic circuit specifically includes sequentially introducing the analyte and buffer, a biological mass amplifier, and a detergent complex from a corresponding number of chambers that are disposed within the microfluidic circuit in order to reduce false positive results detected by the SAW detector.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Figure 1:
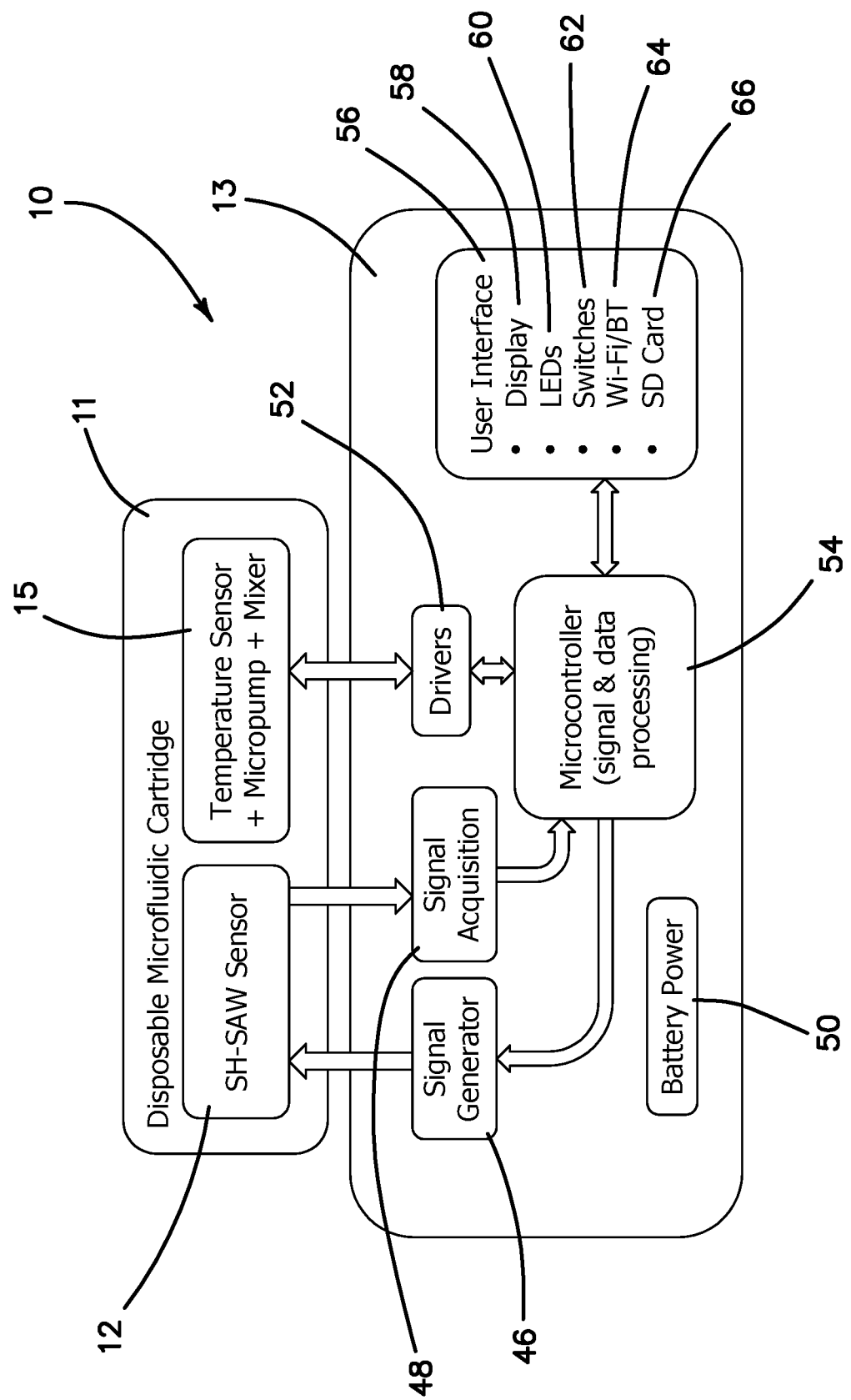
FIG. 1 is a flow diagram of the functional operations of the microfluidic cartridge and the reader of the current invention.

FIG. 1 is a system top level block diagram of microfluidic system 10. Microfluidic system 10 includes a disposable microfluidic cartridge 11 which is inserted into and read by a reader 13. The microfluidic cartridge 11 in turn includes a shear wave surface acoustical wave detector (SAW) 12 and a temperature sensor, micropump and mixer assembly 15. Various embodiments of SAW detector 12 are described in such as described in PCT Patent Application serial no. PCT/US17/48055, entitled Surface Acoustic Wave Biosensor Employing An Analog Front End And DNA Encoded Libraries To Improved Limit Of Detection (LOD) With Exemplary Apparatus Of The Same, filed on 22 Aug. 2017, incorporated herein by reference in its entirety. Reader 13 includes a signal generator 46 that is coupled to and drives SAW 12 and a signal acquisition circuit 48 coupled to SAW 12 for receiving the data signals output by SAW 12. The operation of signal generator 46 and signal acquisition circuit 48 are coupled to microcontroller 54, which provides signal and data processing control subject to software control. Drivers 52 are also coupled to microcontroller 54 and provide the driving and control signals to the elements of the temperature sensor, micropump and mixer assembly 15. User interface 56 is coupled to microcontroller 54 and includes output displays 58, LEDs 60, switches 62, Wi-Fi/Bluetooth connections 64, and secure digital (SD) card connectors 66 as described below. The circuitry of reader 13 is coupled to and powered by a power or battery source 50.

Figure 2:
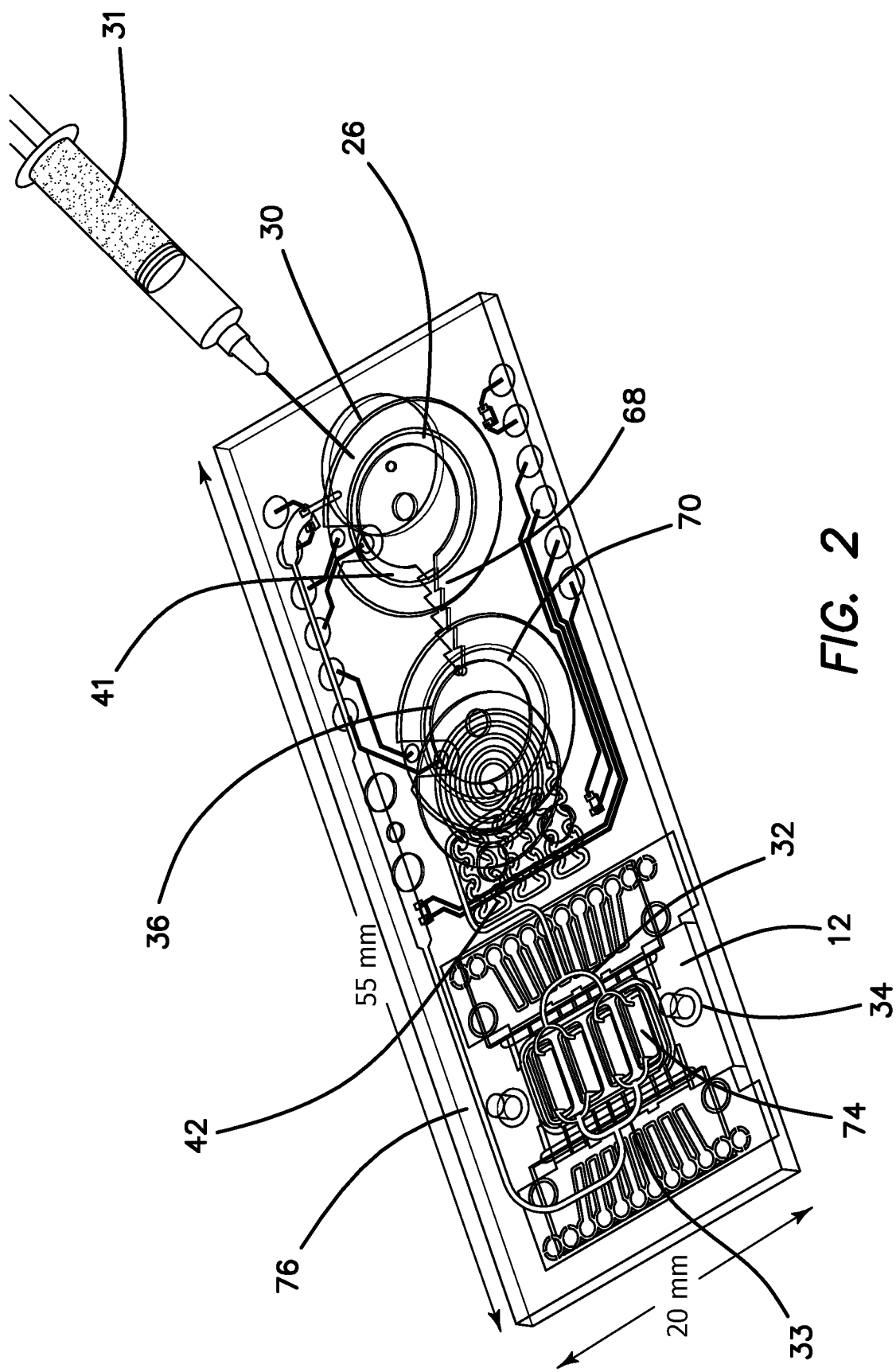
FIG. 2 is a perspective top partial cross-sectional view of the microfluidic cartridge wherein its internal components are shown.

The elements of disposable microfluidic cartridge 11 denoted in FIG. 1 are illustrated in the diagram of FIG. 2. Disposable microfluidic cartridge 11 includes a reservoir chamber 26 in which the analyte 20 is injected in the field through a Tyvek® membrane 30 using a conventional syringe 31 (Tyvek® is a brand of Dupont for flash spun high-density polyethylene fibers). Reservoir chamber 26 includes buffer 24 and is actively mixed with analyte 20 in reservoir chamber 26 by piezoelectric active mixer 41. The mixed buffer 24 and analyte 20, comprising mixture 28, flow through one-way check valve 68 communicated from reservoir chamber 26 to a pump chamber 70 by active of a piezo-pump 36. Pump chamber 70 has a hydrophobic membrane 40 toward which any air bubbles in the mixture 28 are driven and through which the air bubbles escape to ambient atmosphere. The degassed mixture 28 is then pumped into passive mixer 42 to further even the flow rate and mixing. Mixture 28 is then supplied to manifold through which it is supplied to four parallel channels 74 of SAW detector 12 through nozzle-diffuser combination 32. In the illustrated embodiment each channel 74 is approximately 50 µm high, 1.2 mm wide and 4 mm long. One of the channels 74 is a sensing lane 16, while the remaining three channels 74 are reference lanes 17 of SAW detector 12. Sensing lane 16 and reference lanes 17 are identical with the exception that sensing lane 16 is functionalized with a selected antibody 22 according to the analyte 20 which is being detected. The antibody is preferably mass enhanced by the inclusion of a gold nanoparticle, endospore, magnetic beads, or synthetically coupled mass tags linked thereto. Thus, a fraction of analyte 20 will be captured by the functionalized antibodies 22 in sensing lane 16. Any remaining portion of mixture 28, including all nonhybridized analyte 20 from sensing lane 16 and reference lanes 17, are collected in receiving manifold 33 and recirculated through return line 76 to reservoir chamber 26. In the illustrated embodiment, the pumping rate is selected so that the contents of reservoir chamber 26 is recirculated 12 times each minute. A single sampling or measurement is made in microfluidic cartridge 11 once in five minutes. Thus, during a single measurement cycle, mixture 28 is recirculated through microfluidic cartridge 11 sixty times. Effective amplification of the small sample 18 is therefore solved by repetitive recirculation, mixing and cumulative hybridization of analyte 20. The rate of circulation within the microfluidic circuit can vary based on parameter such as pressure drop, Reynolds numbers, viscosity of the medium, temperature, geometrical terms, and analytes conjugation properties (such as K+, K−), and diffusion terms as generally described by the Navier Stoke equation, coupled with the diffusion term.

Figure 3:
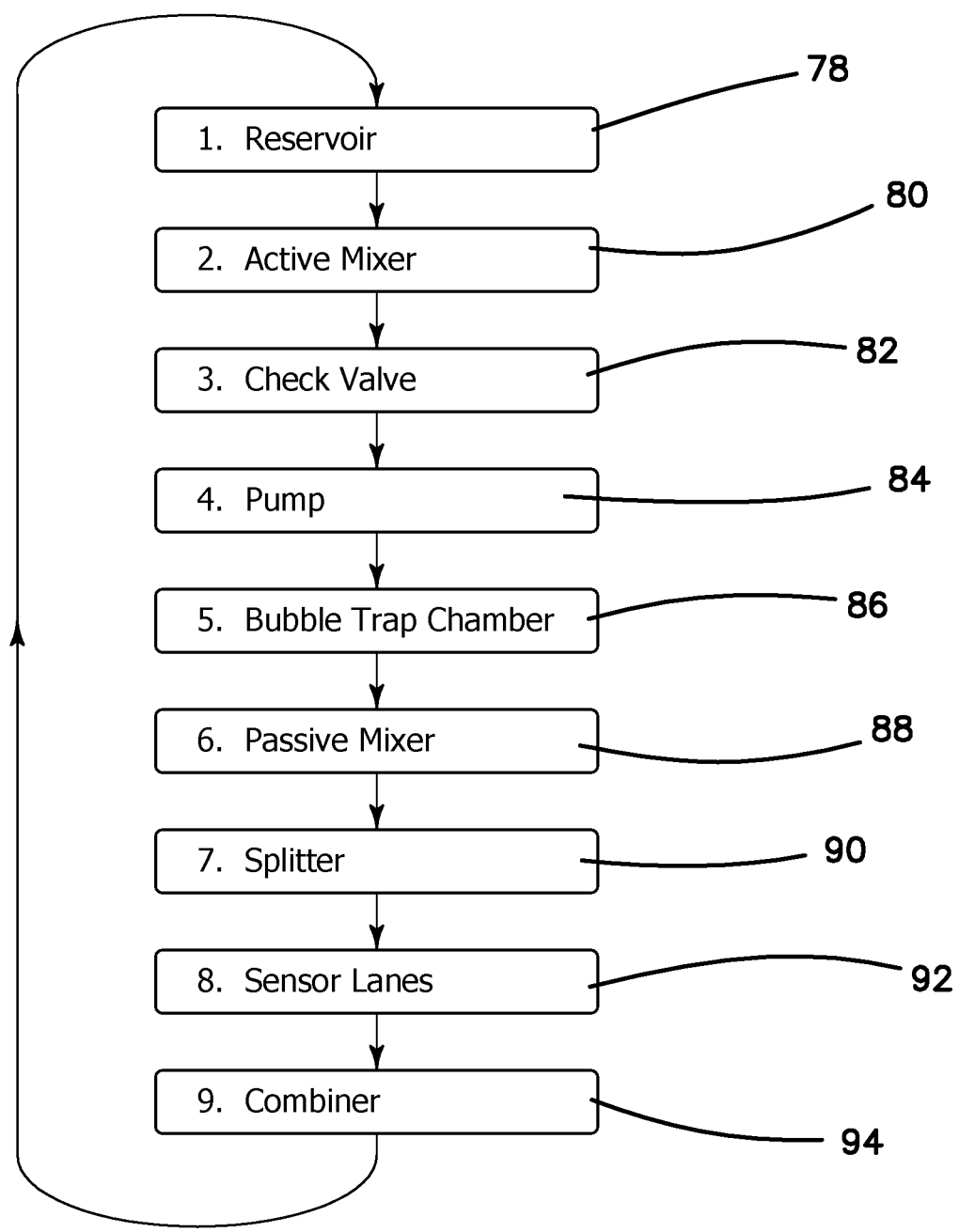
FIG. 3 is a flow chart of the operation of the microfluidic cartridge of the current invention illustrating the recirculation cycle.

The operational phases of microfluidic cartridge 11 can now be better understood by turning to the simplified flow diagram of FIG. 3. Reservoir chamber 26 is loaded in the field with typically 50-100 µL of sample 18 at step 78 from syringe 31 by injection through membrane 30. Active mixer 41 homogenously mixes analyte 20 with buffer 24 in reservoir chamber 26 while the piezo pump 36 positively displaces mixture 28 at step 80 through check valve 68 at step 82. Piezo pump 36 maintains a positive pressure through the entire microfluidic circuit to overcome any pressure drops in the system as denoted at step 84. Mixture 28 enters bubble trap 38 (as seen in FIG. 7) at step 86 and all entrained bubbles are removed from further circulation in the microfluidic circuit. Mixture 28 then flows into passive mixer 42 at step 88, which is a geometric manifold that reduces any remaining inhomogeneity of analyte 20 in buffer 24. Mixture 28 flows into a splitter or nozzle-diffuser combination 32 at step 90 which provides for a balanced distribution of mixture 28 into each of the multiple channels 74 of SAW detector 12. Mixture 28 then flows through sensing lane 16 and reference lanes 17, where the confining 50 µm channel height assures uniform flow across the width of sensing lane 16 at step 92. After exiting channels 74 mixture 28 from each of the channels 74 is combined in receiving manifold 33 and returned under pressure in return line 76 to reservoir chamber 26 at step 94.

Figure 4:
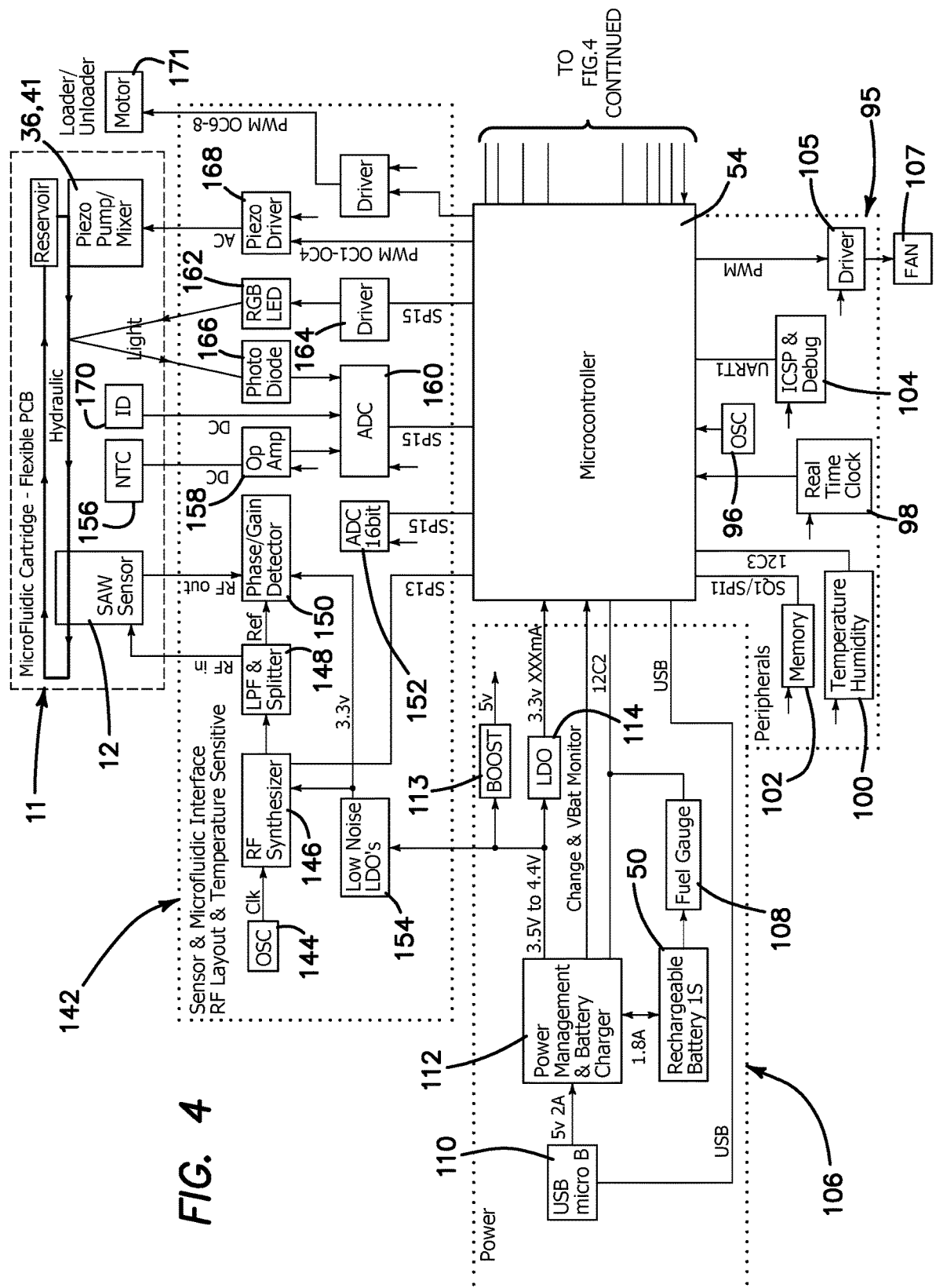
FIG. 4 is a block diagram of the electronic components of the microfluidic cartridge and reader of the current invention.
Figure 4:
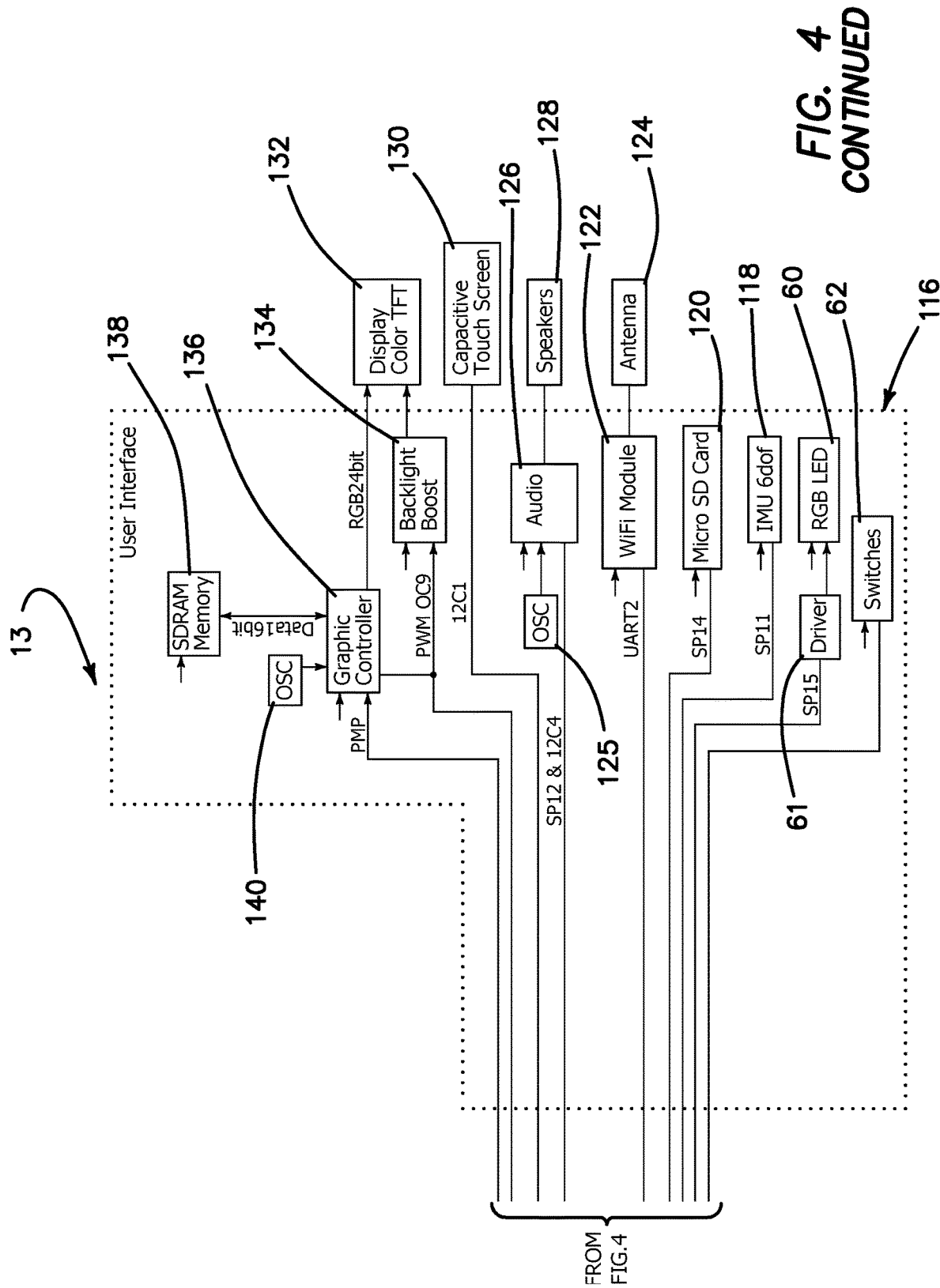

FIG. 4 is a simplified block diagram of the circuitry in microfluidic cartridge 11 and reader 13. The circuitry of reader 13 is logically centered around microcontroller 54, which includes related peripherals 95 such as oscillator 96, a real-time clock 98, an on-board temperature sensor 100, memory 102, in-circuit serial programming (ICSP) module 104, and driver 105 coupled to cooling fan 107, all of which are coupled to microcontroller 54.

A power module 106 is also coupled to microcontroller 54 and includes battery source 50, fuel gauge 108 coupled between battery 50 and microcontroller 54, universal serial bus (USB) connector 110 coupled to power management integrated circuit (PMIC) 112 having one output coupled to a low drop out regulator (LDO) 114 and hence all coupled to microcontroller 54. PMIC 112 is also coupled to battery source 50 for charge and voltage monitoring and boost 113 for providing for a boosted DC voltage.

A user interface 116 is coupled to microcontroller 54 and includes in the illustrated embodiment program switches 62, output LEDs 60 with connected driver 61, a six-degrees of freedom inertial measurement unit (IMU) 118 employed by the apparatus to adjust for flow rate relative to gravitational vector in regiments where an orthogonal gravitational vector cannot be achieved is coupled through a serial peripheral interface bus, as is a secure data (SD) card connector 120. A Wi-Fi module 122 is coupled to microcontroller 54 through a universal asynchronous receiver/transmitter (UART) bus, whose output is coupled in turn to an antenna 124 to allow wireless communication by microfluidic system 10 with the internet or other computer network. An oscillator 125, coupled to audio module 126, is coupled to microcontroller 54, whose output in turn is coupled to a speaker 128 so that microfluidic system 10 can communicate with the user through audio messages. Microcontroller 54 is also coupled to a capacitive touch (CAP) display 130 to allow screen touch communication with the user. A thin-film transistor (TFT) color display 132 which is backlight by light 134 is coupled to microcontroller 54 through graphic controller 136, which in turn is supported by an oscillator 140 and synchronous dynamic random access (SDRAM) memory 138 coupled thereto.

As further seen in FIG. 4, a SAW interface 142 is also coupled to microcontroller 54 to provide a control interface between microcontroller 54 and microfluidic cartridge 11. Oscillator 144 provides a clock signal to RF synthesizer 146, whose output is passed through a low pass filter and splitter 148 to drive SAW detector 12. A reference signal is supplied from low pass filter (LPF) and splitter 148 to phase/gain detector 150 coupled to the output of SAW detector 12. The output of phase/gain detector 150 is converted into digital form by analog-to-digital converter (ADC) 152 and provided to microcontroller 54 as the data signal through a serial data bus. Power is provided from PMIC 112 to low noise low drop out regulator (LDO) 154 to RF synthesizer 146 and phase/gain detector 150. The temperature of mixture 28 in microfluidic cartridge 11 is measured by negative temperature coefficient thermistor (NTC) 156 and provided through operational amplifier 158 to analog-to-digital converter (ADC) 160 and hence to microcontroller 54. Photometric measurements are made possible of mixture 28 by means of an RGB LED 162 powered by driver 164 controlled by microcontroller 54. The incoming optical signal is directed to widened optical channel 77 best shown in FIG. 5 in return line 76 by which optical sensing of the recirculating fluid flow can be measured. The returned optical signal is received by photodiode 166, whose output is digitized by ADC 160 and provided to microcontroller 54. The light absorption spectra received from the recirculating analyte is generating a spectral shift proportional to the absorption rate due to protein or any circulating component within the channel. The resulting signal indicates whether the recirculating analyte are passing through the channel while the microcontroller records the optical signal indicating the presence, or lack thereof, of analyte within the channel. One skilled in the relevant art can conceive of an alarm signal and intelligent data gathering associated with such an embodiment as it indicates the presence of suspended analyte concentration. Piezo pump 36 and active mixer 41 in microfluidic cartridge 11 are driven by piezo driver 168 controlled by microcontroller 54. Microfluidic cartridge 11 may also include a biological identification module 170 coupled to microcontroller 54 through ADC 160 by which identification information specific to microfluidic cartridge 11 is read. This safety feature enables a clear distinction by identifying the analyte specificity with a resistor value registered by the resident memory 102 and provides the reader with an analogue distinction of what specific antigen concentration is being recorded. A driver 169 is coupled to microcontroller 54 and thence to a motor 171 for providing for motorized loading of microfluidic cartridge 11 into a cartridge holder 173 for automated and uniform connection of microfluidic cartridge 11 to reader 13.

Figure 5:
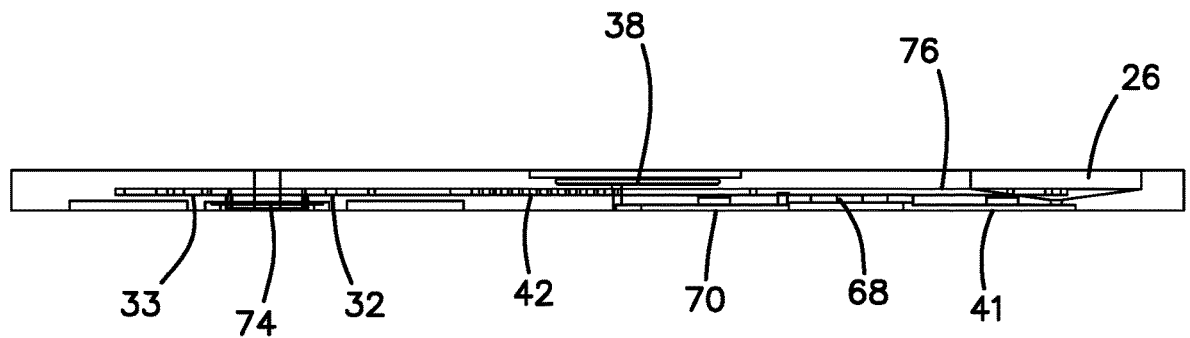
FIG. 5 is a longitudinal side cross-sectional view of the microfluidic cartridge seen in FIG. 2 illustrating the three levels of structure of the cartridge.
Figure 6:
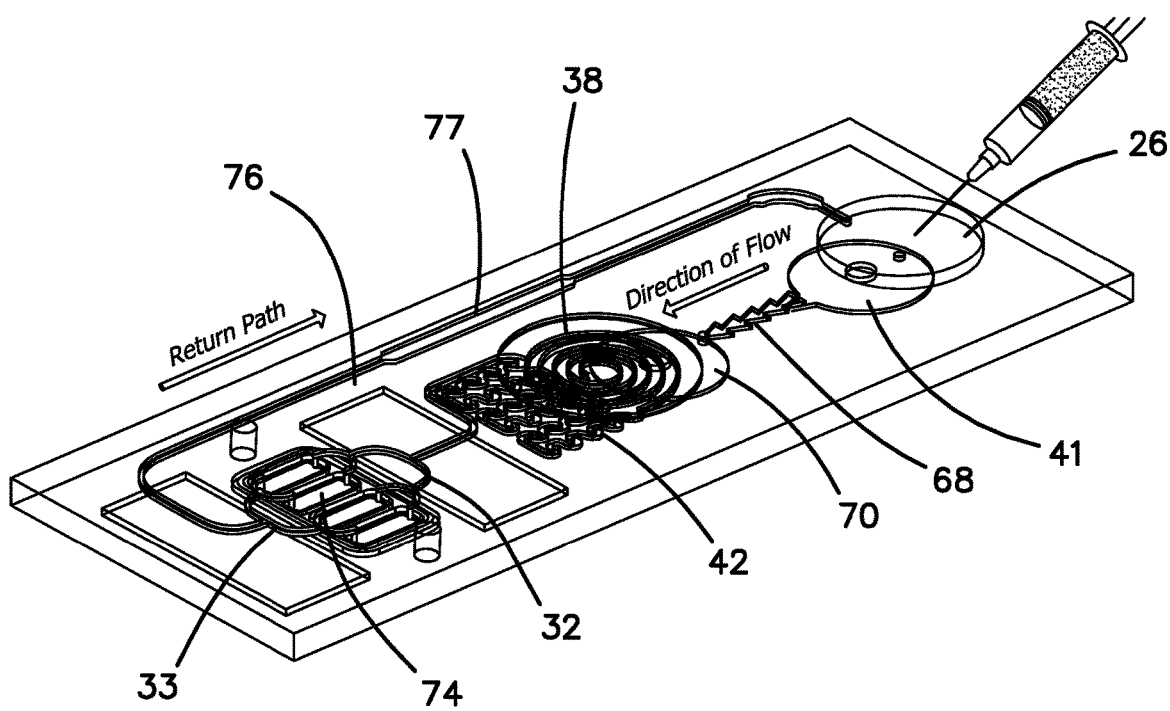
FIG. 6 is a simplified top perspective partial cross-sectional view of the microfluidic cartridge seen in FIG. 5 illustrating the combination of components employed in the recirculation protocol.

The arrangement of microfluidic cartridge 11 can be better appreciated by comparing FIGS. 5 and 6, wherein the three levels of the flow path structure of microfluidic cartridge 11 can be visualized. FIG. 5 is a side cross sectional view of microfluidic cartridge 11 and FIG. 6 is a top perspective view of microfluidic circuit in the cartridge 11. The top level includes reservoir chamber 26 and spiral bubble trap 38. Beneath the top level is a middle level which includes passive mixer 42, splitters or manifold 32, receiving manifold 33 and return line 76. Beneath the middle level is the bottom level which includes active mixer 41, check valve 68, pump chamber 70, and channels 74. Thus, it can readily be understood and visualized that the mixture 28 starts in reservoir chamber 26 in the top level and is drawn down into active mixer 41 in the bottom level from where it flows up through check valve 68 in the middle level into pump chamber 70 in the bottom level. Mixture 28 then flows up to the spiral bubble trap 38 in the top level and after being de-bubbled flows back down into the middle level of passive mixer 42. Mixture 28 continues to flow to manifold 32 in the middle level and thence is distributed to channels 74 of SAW detector 12 in the bottom level. From channels 74 mixture 28 is then pumped into receiving manifold 33 and along return line 76 in the middle level to reservoir 26 in the top level.

Figure 7A:
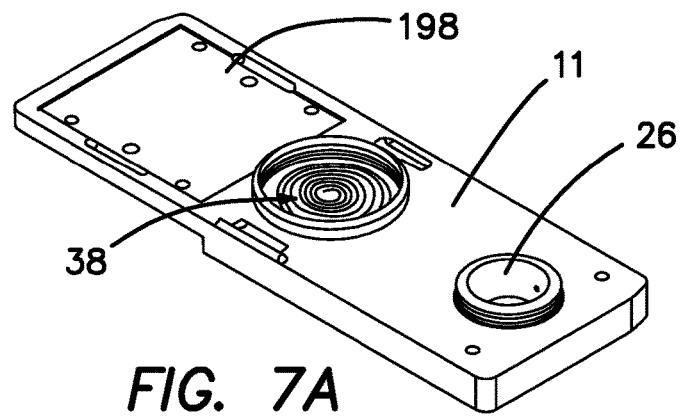
FIG. 7A is a top perspective view of the microfluidic cartridge seen in FIG. 2.
Figure 7B:
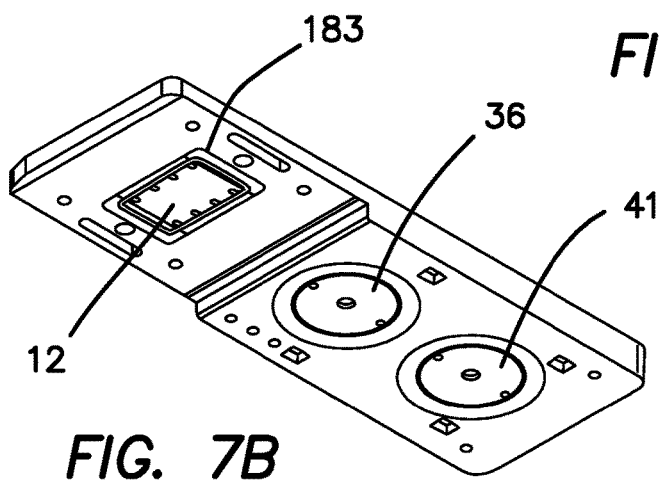
FIG. 7B a bottom perspective view of the microfluidic cartridge seen in FIG. 7A.
Figure 7C:
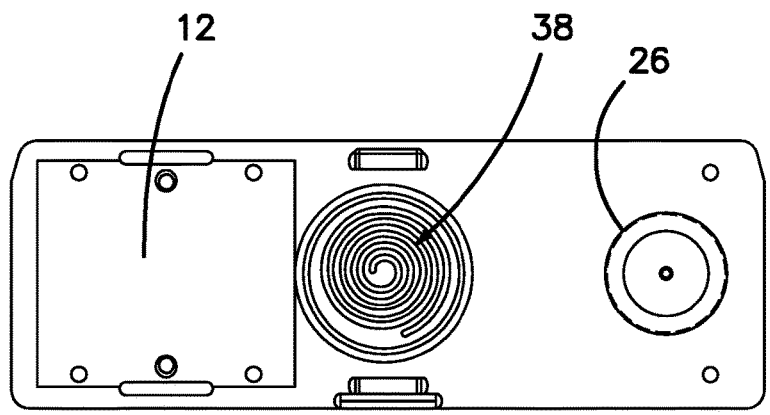
FIG. 7C a top plan view of the microfluidic cartridge seen in FIG. 7A.
Figure 7D:
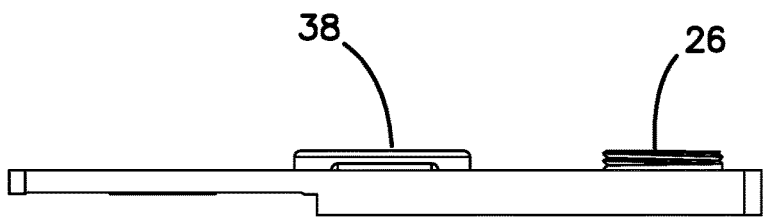
FIG. 7D a side planar view of the microfluidic cartridge seen in FIG. 7A.

FIGS. 7A-7D show the externally visible components of the cartridge 11, showing in FIGS. 7A, 7C and 7D the de-bubble chamber 38. FIG. 7A further depicts top RF shield area 198, while FIGS. 7C and 7D show the reservoir 26. FIG. 7B shows gasket gland 183, pump 36 and active mixer 41.

Figure 8:
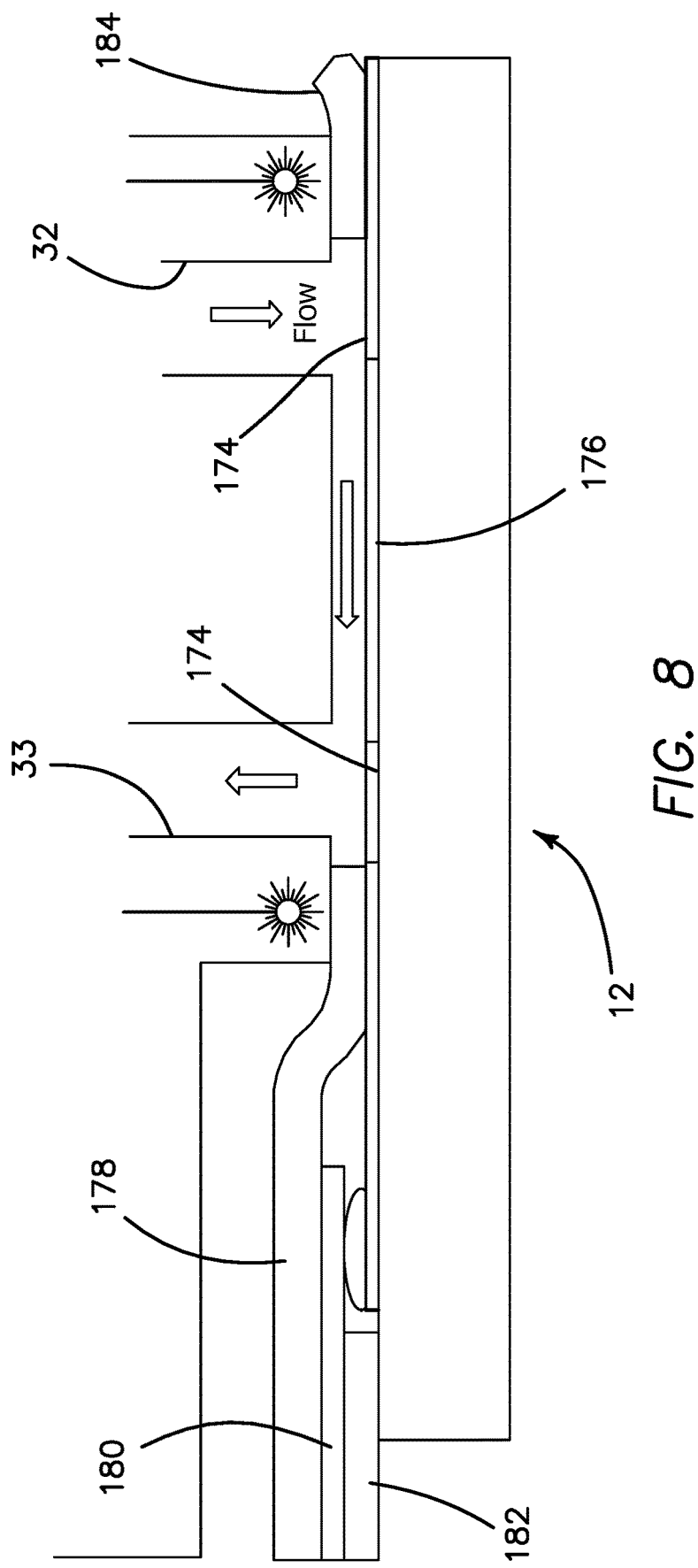
FIG. 8 is a partial side cross-sectional view of microfluidic cartridge showing the relationship of the manifolds, the SAW detector, and the printed circuit board used within the microfluidic cartridge.

FIG. 8 is a side cross sectional view in enlarged scale of the SAW detector 12 bonded underneath and laser welded to the corresponding adjacent portions of microfluidic manifolds 32 and 33 of microfluidic system 10, which in the illustrated embodiment are made of cyclic olefin copolymer. SAW detector 12 is a conventional LiTaO$_3$ substrate cut for Love Wave propagation with opposing piezo interdigitated transducers (IDT) 174 on each end of a surface waveguide 176 on which are provided sensing lane 16 and reference lanes 17. The flexible printed circuit board 184 to which SAW detector 12 is adhesively coupled includes a 50 μm Kapton® top layer 202 (Kapton® is a mark of Dupont De Nemours and Co. Corp. of Delaware) underneath which is 35 μm copper cladding 203 followed by a 50 μm Coverlay® bottom layer 204 (Coverlay is a registered mark of Coverlay Mfg Inc. of Texas). Printed circuit board 184 continues from the right end of the partial view of FIG. 8 to include conventional mounting locations for the remaining electrical elements of microfluidic cartridge 11 as described above and for RF ground shielding 198 for SAW detector 12.

Figure 9:
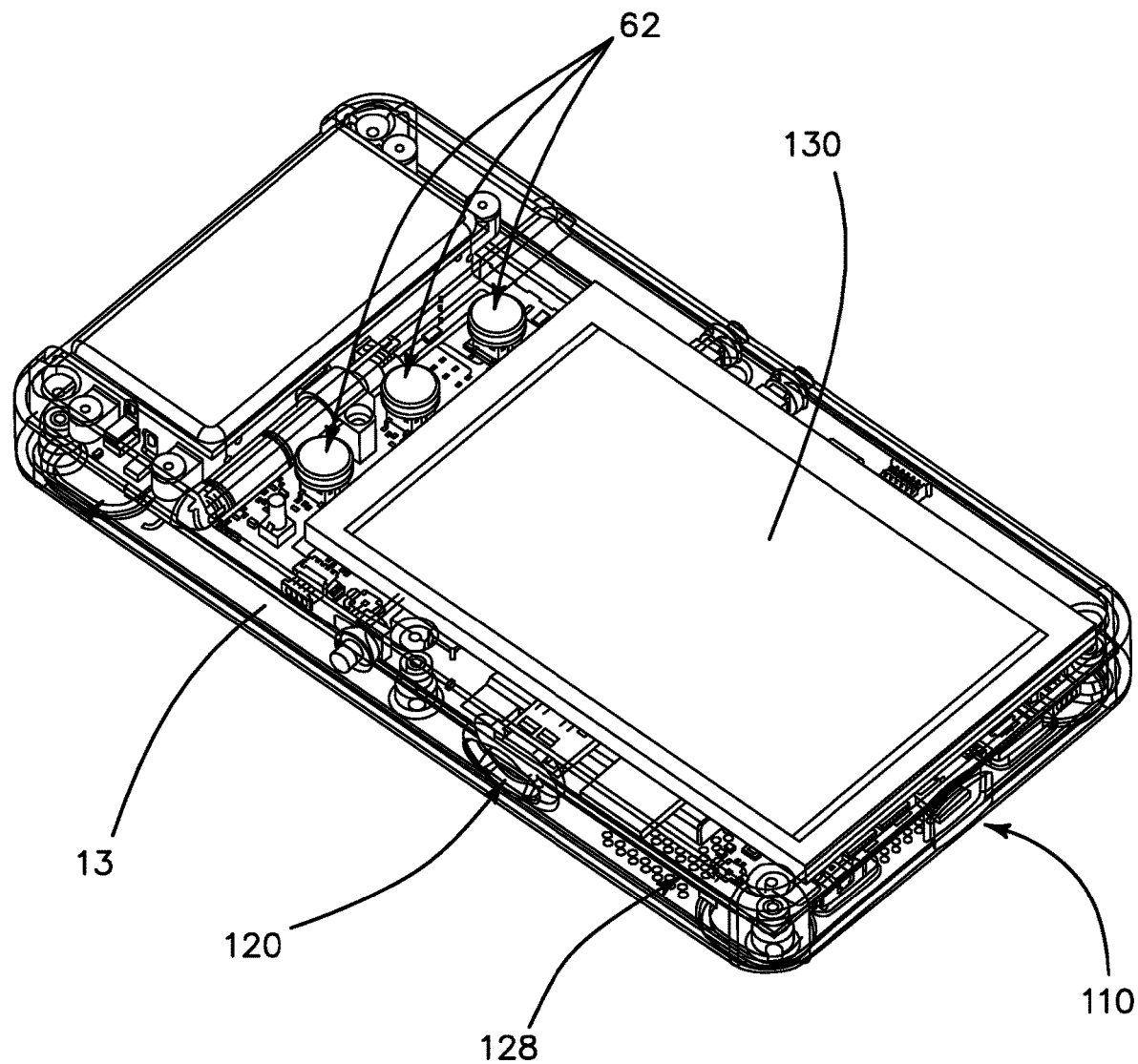
FIG. 9 is a top down perspective view of the internal components of the portable handheld field assay of the current invention.

FIG. 9 is a perspective view of one embodiment of the field portable reader 13 into which microfluidic cartridge 11 is inserted. In the illustrated embodiment reader 13 is similar in size to a conventional cell phone, namely 25 mm thick, 180 mm long and 100 mm wide. Most of the upper top surface is occupied by the capacitive touch screen 130. Microfluidic cartridge 11 is inserted into a conventional side slot loading receiver (not shown) similar to a slot loading DVD drive in a conventional laptop computer. In this manner, microfluidic cartridge 11 is uniformly handled or loaded into reader 13 and shielded or isolated from the environment without undue force or stress applied thereto and without electrode or contact misalignment errors that might result from manual handling by an untrained user. The user interfaces with the device through a series of buttons 62 that control menu features. For output of data, there exists an SD card reader 120, a micro-usb output port 110 and a speaker 128.

Figure 10:
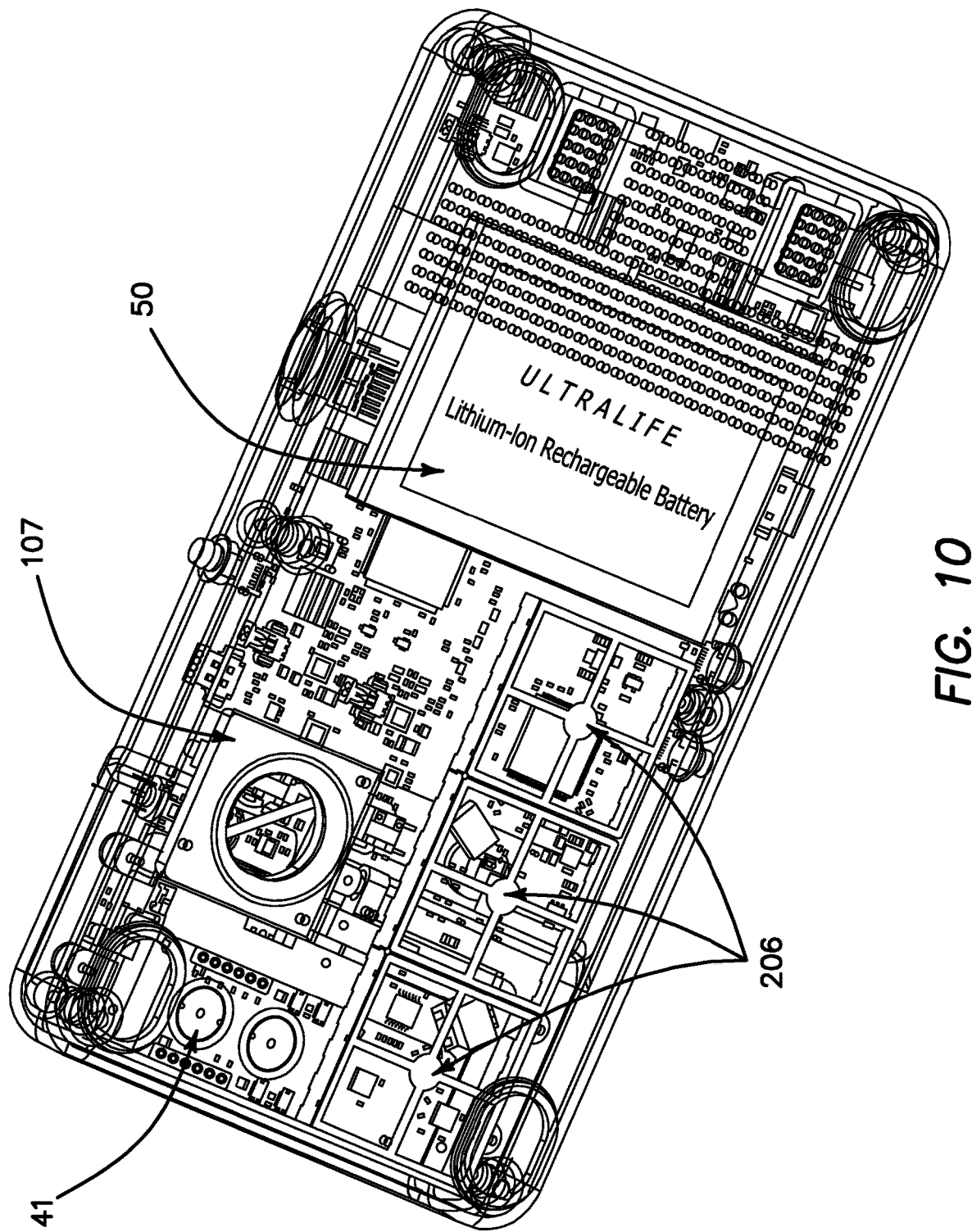
FIG. 10 is a bottom up perspective view of the portable handheld field assay seen in FIG. 9.

FIG. 10 is a perspective view of microfluidic system 10 from the bottom showing the placement of the battery 50, RF shields 206, active mixer 41 and the fan component 107.

Figure 11A:
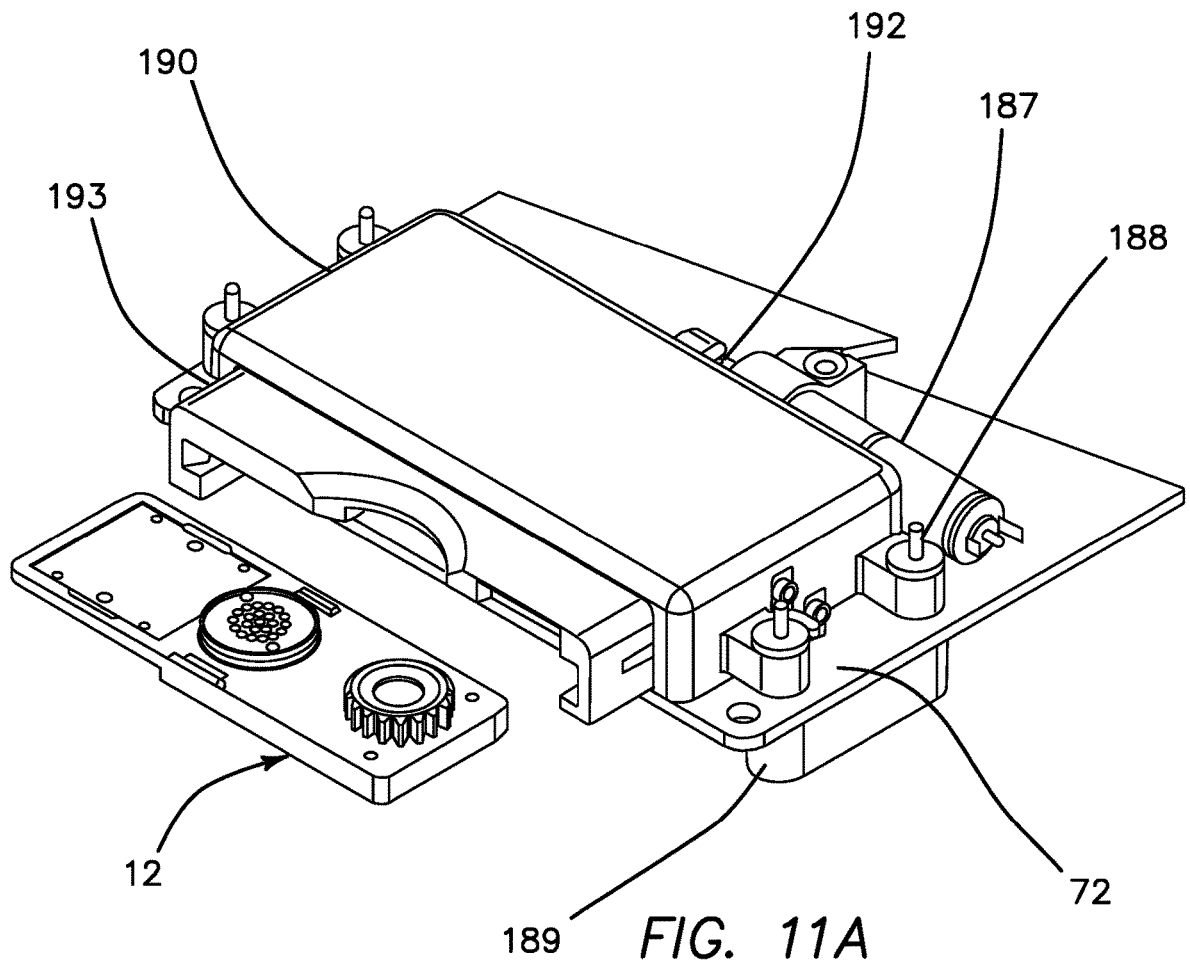
FIG. 11A is a top perspective view of the cartridge loader/carrier and its mechanical components.
Figure 11B:
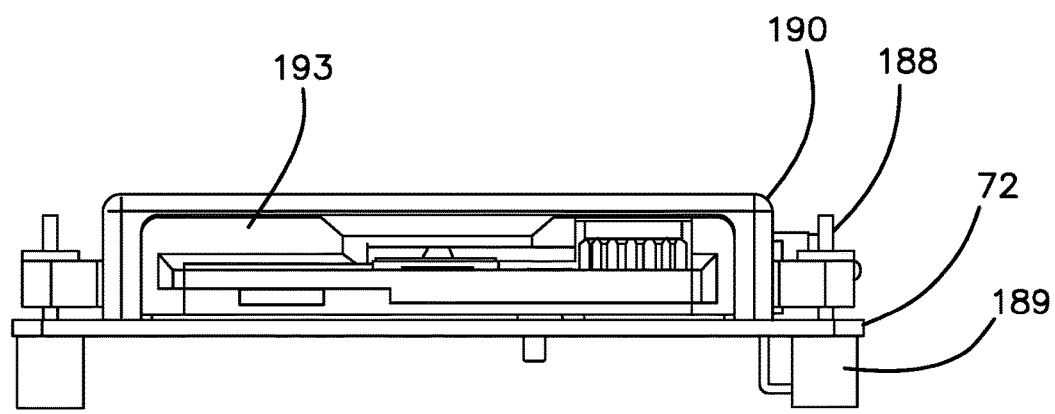
FIG. 11B is a side plan view of the cartridge loader/carrier and its mechanical components seen in FIG. 11A.

FIG. 11A is a perspective view of the cartridge loader 190 and uninserted cartridge carrier 193. Incorporated into the cartridge loader 190 is a Maxton motor 187 and motor cam 192 for motorized loading and unloading of the cartridges 11. The mechanism is attached by dowel pins 188 to a dowel pin base 189 which binds the apparatus to the PCB assembly 72. FIG. 11B is a side plan view of the cartridge loader 190 with the cartridge carrier 193 inserted therein.

Figure 12:
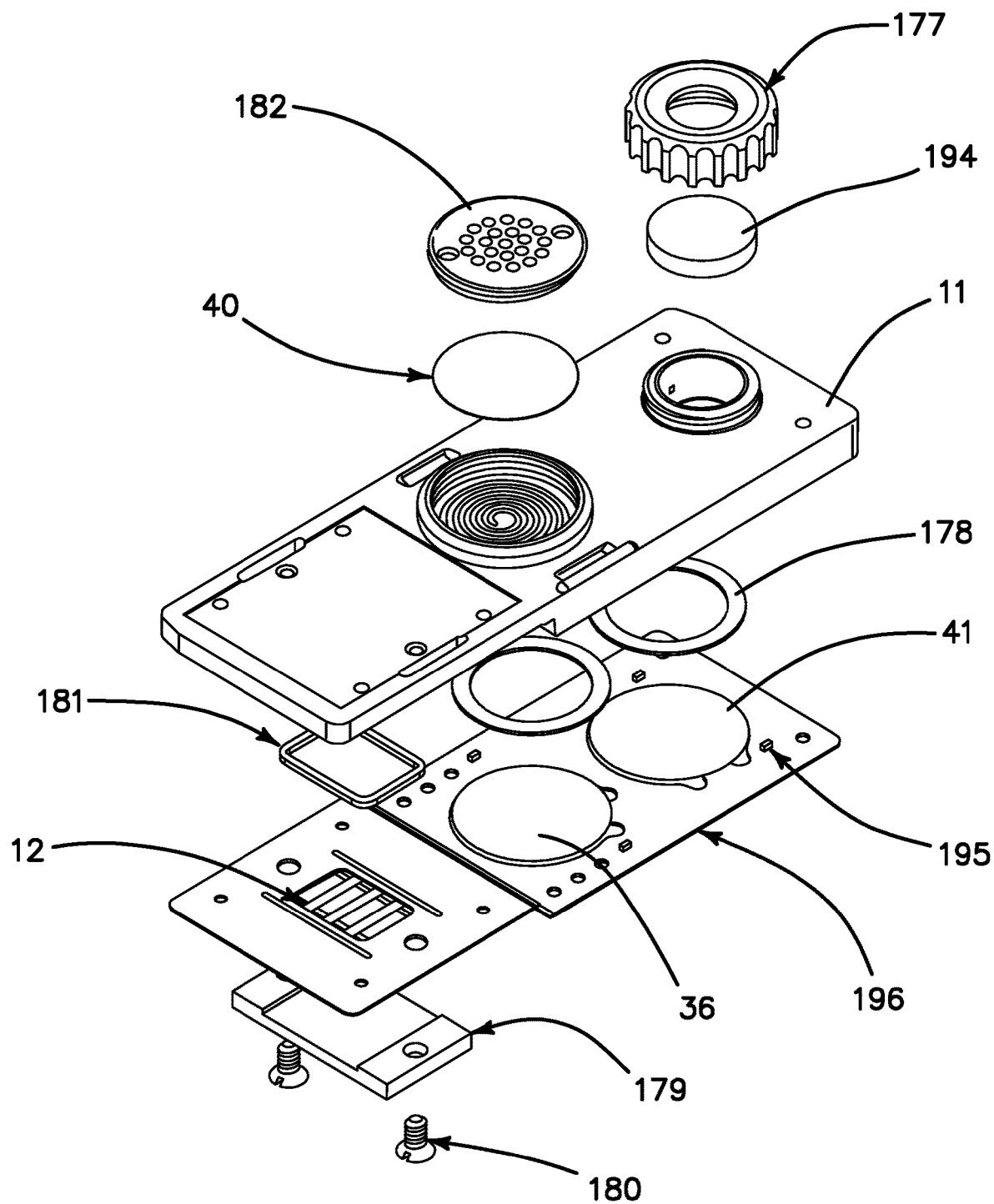
FIG. 12 is an exploded perspective view of the microfluidic cartridge showing seen in FIG. 2.

FIG. 12 shows the microfluidic components of the cartridge 11. The reservoir cap 177 fits over the septum 194 to retain sample 18. The de-bubble cap 182 is placed on top of the hydrophobic filter 40 to reduce the number of bubbles that reach SAW 12 surface and effect diffusion timescale. Two piezo seals 178 are incorporated into the active mixer 41 and piezo pump 36 to maintain a closed circuit. SAW 12 is attached to the cartridge 11 by placement on a FPC 196 that holds both the piezo pumps 36, 41 and corresponding chips. Temperature variation is monitored by thermistor 195 reporting to microcontroller 54 as to the actual temperature of the cartridge during the operation and where the microcontroller lookup table residing in memory 102 adjust the flow rate in accordance with Navier Stoke equation. A gasket 181 ensures no sample 18 escapes at the SAW 12 site. A SAW compression bar 179 holds the SAW 12 firmly to the gasket 181, and is held down by two screws 180.

Figure 13A:
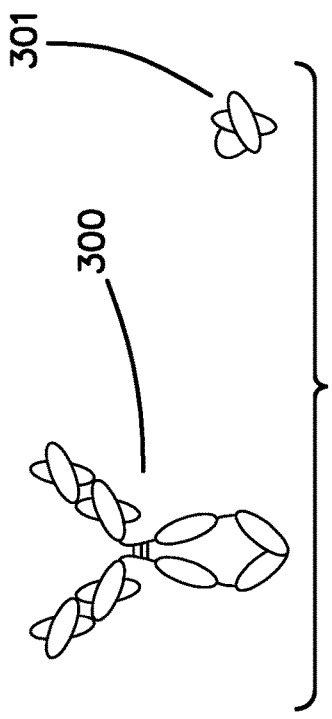
FIG. 13A is an illustration of a comparison of whole IgG with F(ab')2 and scFv fragments used for biological mass amplification for SH-SAW biosensor technology.
Figure 13B:
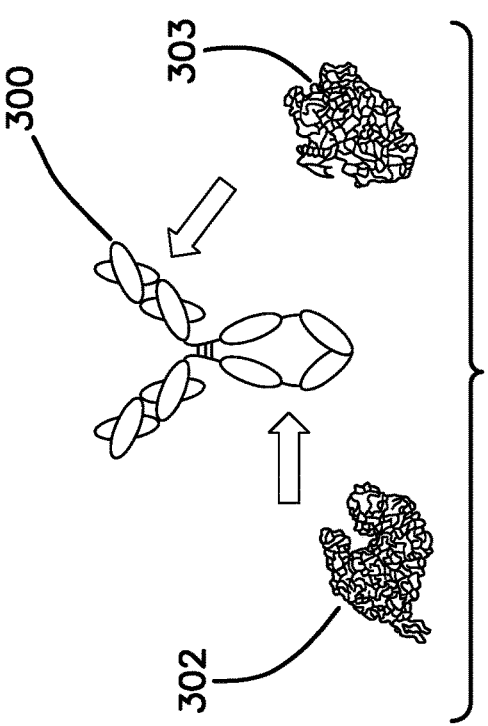
FIG. 13B is an illustration of common linker proteins used to bind IgG and scFv fragments used for biological mass amplification for SH-SAW biosensor technology.
Figure 13C:
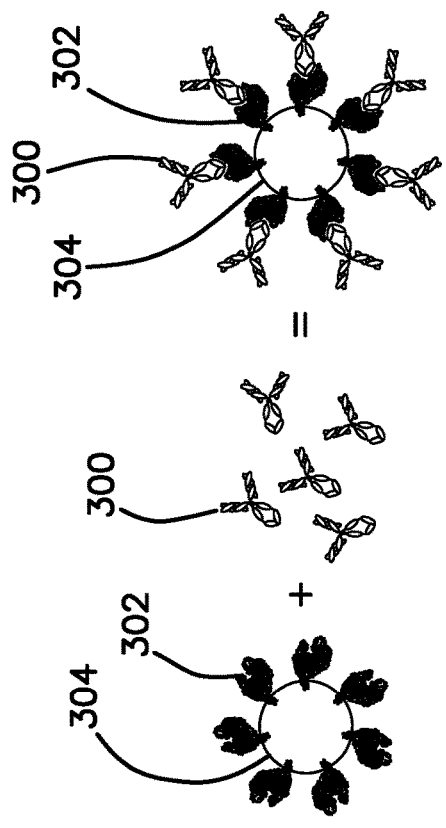
FIG. 13C is an illustration of an endospore display system used to bind any IgG or scFv for mass amplification.
Figure 13C:
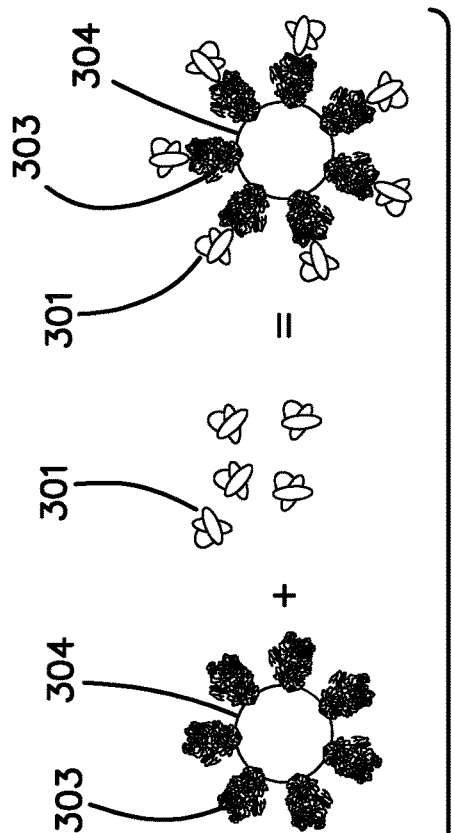
Figure 14B:
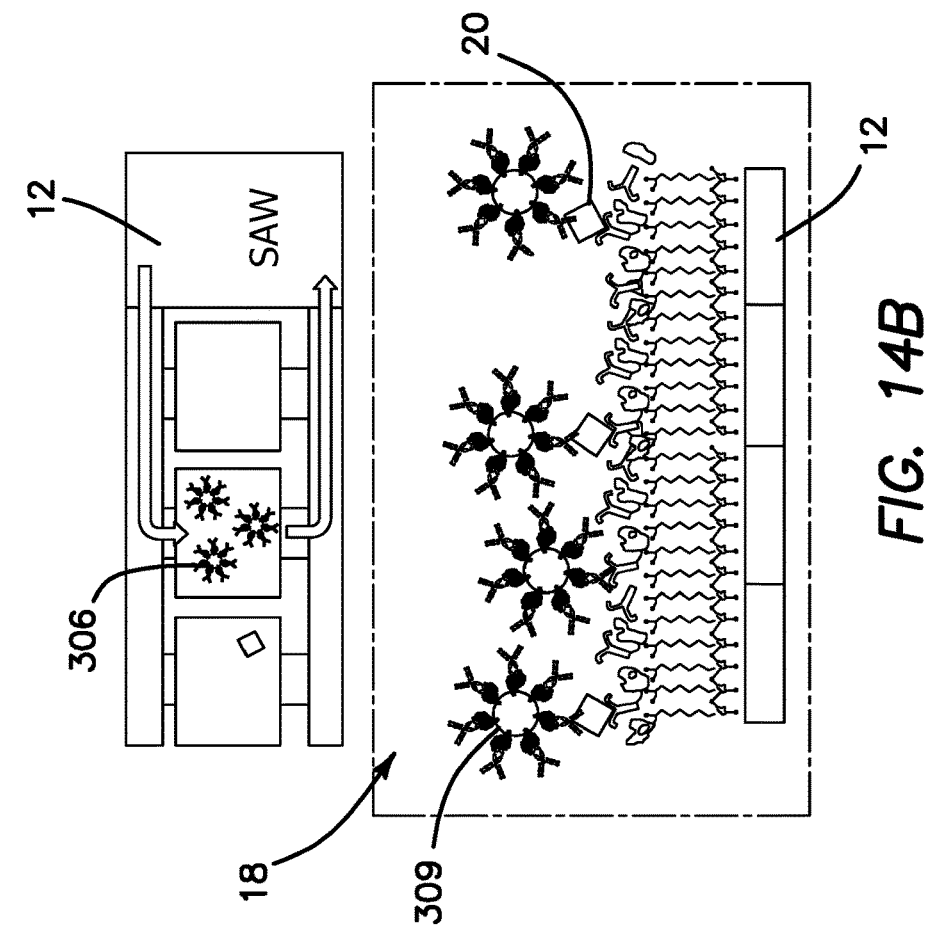
FIG. 14B is a flow diagram illustrating the delivery of a biological mass amplifier using recirculation within a multi-reservoir system and a magnified view of the biological mass amplifier interacting with the analyte.
Figure 14A:
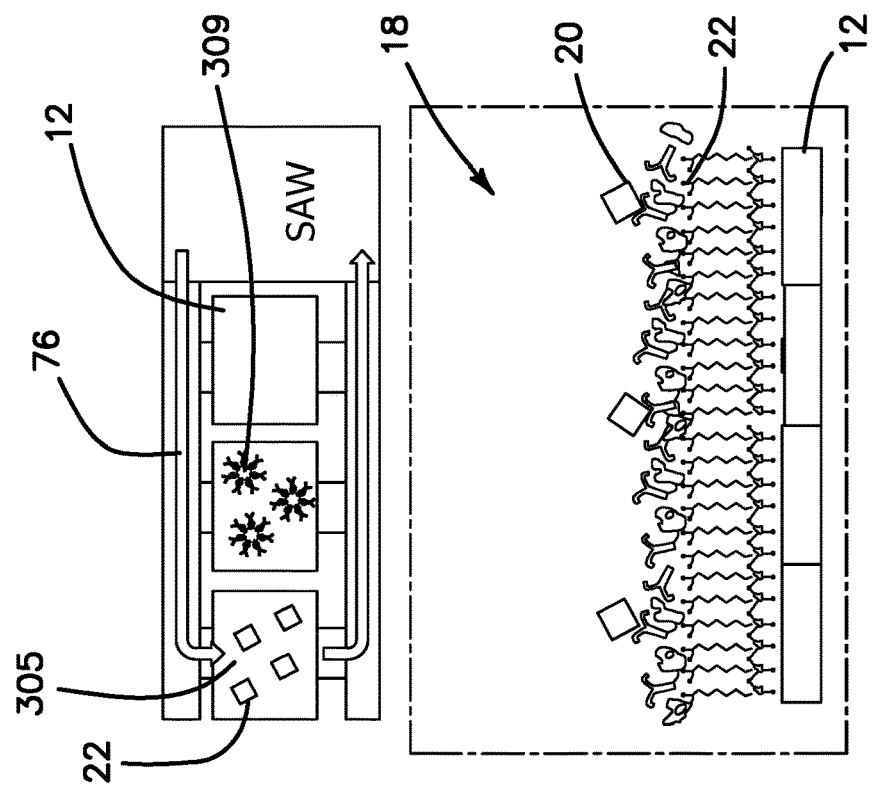
FIG. 14A is a flow diagram illustrating the delivery of an analyte using recirculation within a multi-reservoir system and a magnified view of the analyte interacting with an antibody disposed on the SAW of the current invention.
Figure 14C:
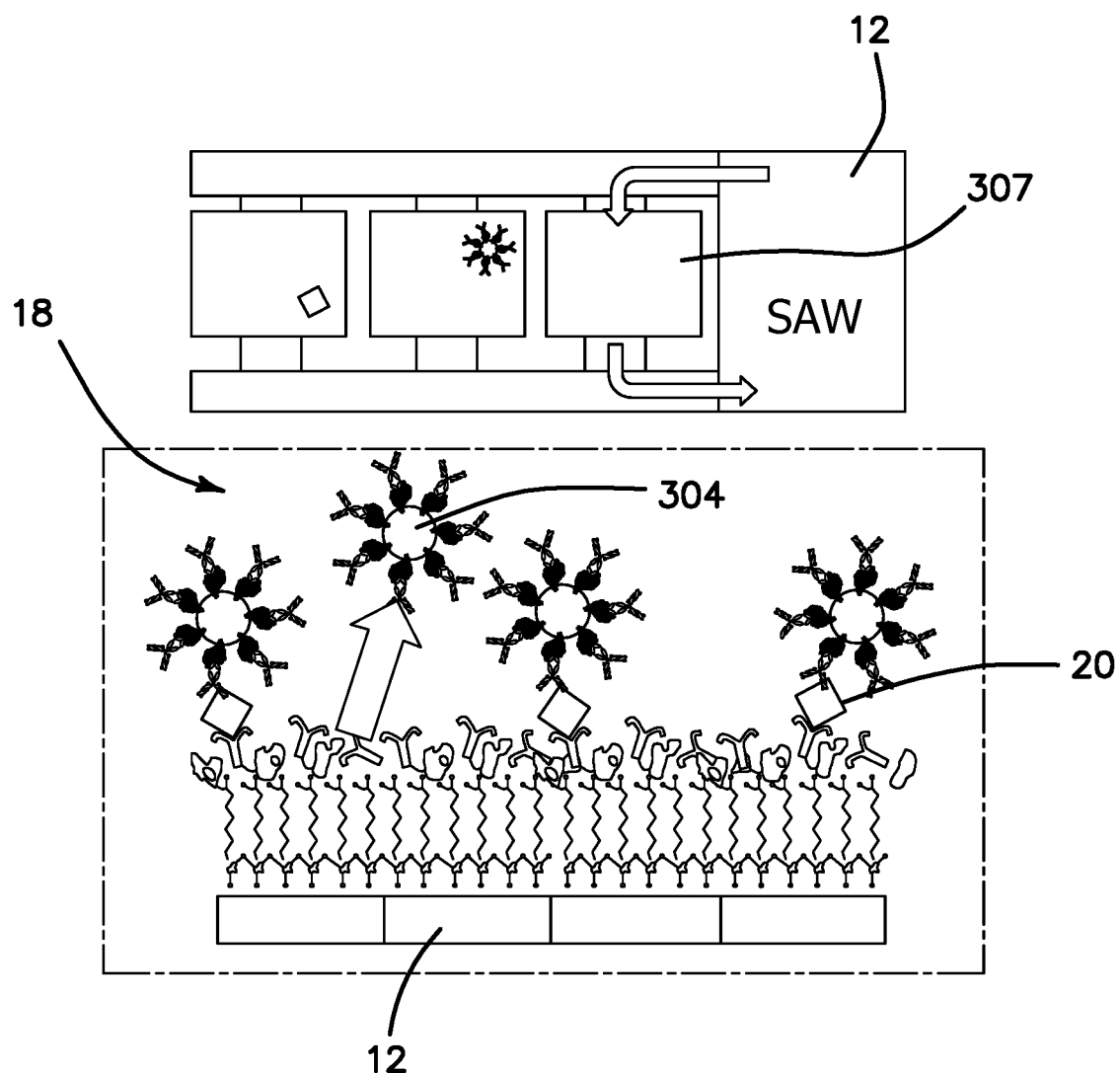
FIG. 14C is a flow diagram illustrating the delivery of dilute detergent to wash off non-specifically bound entities using recirculation within a multi-reservoir system and a magnified view of excess biological mass amplifier being removed from the SAW.
Figure 15A:
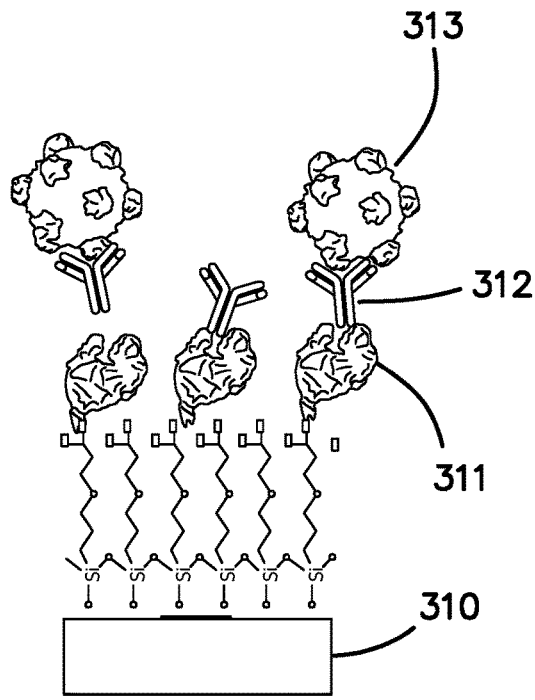
FIG. 15A is an illustration of protein-G orientation-enabled detection of engineered PhiX174-HA virus using the microfluidic cartridge of the current invention.
Figure 15B:
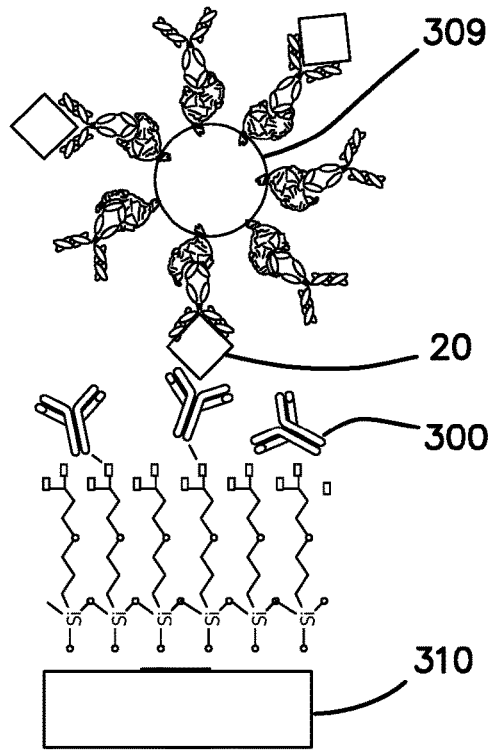
FIG. 15B is an illustration of detection of all-purpose endospore resulting in mass amplification using the microfluidic cartridge of the current invention.
Figure 15C:
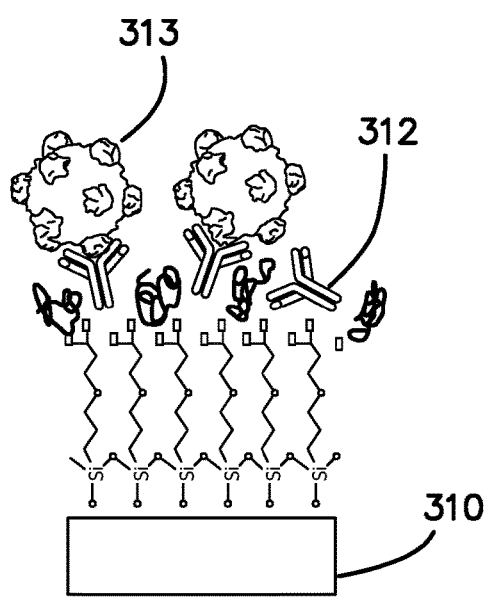
FIG. 15C is an illustration of a simplified strategy for detection of PhiX174-HA virus for initial studies using the microfluidic cartridge of the current invention.
Figure 15D:
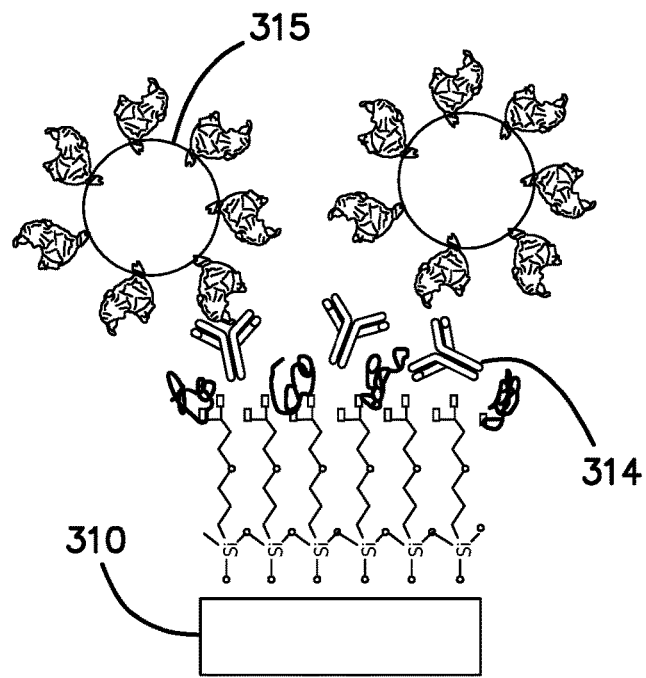
FIG. 15D is an illustration of a simplified strategy for detection and proof-of-concept of endospore-enabled mass amplification for initial studies using the microfluidic cartridge of the current invention.

FIG. 13a is a graphical representation of the capture and detection technique employed by the invention whereby a comparison between complete antibodies 300 and scFv fragmented antibodies 301. FIG. 13B indicate how protein A 302 interacts with the complete antibodies 300 and protein L 303 interacts with scFv fragmented antibodies 301. FIG. 13C illustrates how endospores 304 are generated to either express protein A 302 or protein L 303 depending on the capture application, as well as an ELISA chain consisting of an endospore 304, and either protein A 302 and a complete antibody 300 or protein L 303 and a fragmented antibody 301 are conjugated.

FIGS. 13A-13C further illustrate the bio-amplification and mass enhancement endospore 304 of the analyte 20, while illustrating the biochemical sequencing-events performed automatically by the microfluidic chamber 14 and directed by the Reader 13. The strategy to develop all-purpose endospore display system for biological mass amplification for SH-SAW biosensor technology is the purpose of the current invention and it comprises the example shown in FIG. 13A where there is a graphic representation and a comparison of whole IgG antibody with F(ab')2 300 and scFv fragments 301. FIG. 13B is a graphical representation of a common linker proteins 302 and 303 used to bind IgG and scFv fragments. FIG. 13C demonstrates a bio-amplification technique where an endospore 304 display system is used to bind any IgG 300 or scFv 301 for mass amplification purposes. The technique noted above relates to the fact that concentration of analyte at the range of femtogram to picogram per $ml^{-1}$ are below threshold resolution of the SAW 12 and the amplification of mass is a necessary step to obtain a measurement at this range. The ability of the preferred embodiment to measure such concentrations and the use of bio-amplification while obtaining results commensurable with clinical values is main purpose of the current invention.

FIGS. 14A-14C are graphical representations of the preferred embodiment of the SAW 12 whereby a three stage convection enhanced delivery (CED) mechanism that contains the analytes 22 in sample 18 is introduced into chamber 305. In the first step seen in FIG. 14A, the analytes 22 are being recirculated through the reservoir sample complex to the SAW 12 and returned through the return line 76. The next step in FIG. 14B shows the utilization of the reservoir endospore complex 309 to administer the biological mass amplifier Ab-conjugated r scFv conjugated endospores, or any other functionalized mass amplifying particles, from chamber 306 over the SAW 12. The final step in FIG. 14C shows the reservoir detergent complex from chamber 307 being administered to dilute detergent and wash off any non-bound endospores 304 from the SAW 12.

FIG. 15A is a schematic representation and example of a bio-amplification technique used by the current invention demonstrating the ability of mass amplification to employ multiple techniques of adding mass to the SAW 12 employing, for example, viruses such as PhiX174-HA virus 313. Displayed is an initial design of protein-G 311 orientation-enabled detection of an engineered PhiX174-HA virus 313 through an ELISA chain consisting of the silane surface 310, protein G, capture antiHA antibody 312, and the target PhiX174-ha 313. FIG. 15B illustrates the detection using endospore 304 display mass amplification through the creation of an ELISA chain consisting of a silane 310 surface, capture antibody 300, analyte 20, and the Ab-Conjugated or scFv-conjugated endospore 309. FIG. 15C shows a simplified strategy for detection of PhiX174-HA virus 313 for initial studies consisting of a silane surface 310, and capture antiHA antibody 312 and the target PhiX174-HA virus 313. FIG. 15D shows a simplified strategy for detection and proof-of-concept of endospore 304 enabled mass amplification for initial studies consisting of an ELISA chain of silane 310, COTB capture antibody 314, and CotB amplified endospore 315. It is understood that further mass amplification sandwich techniques such as using functionalized magnetic beads, synthetically generated mass tags, gold nano particles, viruses, microphages or bacteriophages, or any other suitable mass employing an ELISA like sandwich method may be used without departing from the original spirit and scope of the invention.

The current invention improves the sensitivity of biosensor platforms such as those outlined above. The embodied biosensor technology can assess real-time surface interactions between an antibody and an antigen associated with a disease state or environmental contaminant. The biosensor platform measures attenuation of traveling shear-horizontal surface acoustic waves (SH-SAW) caused by the accumulation of mass of bound antigens to the sensing area functionalized with a target-specific protein molecule. There are four guiding design principles for the current invention: time, limit of detection (LOD), high signal-to-noise (SNR), and portability. To achieve these design objectives, the invention is divided into two core areas of focus: capture of the analyte from solution, and the detection of the analyte via the SAW sensor.

A typical SH-SAW biosensor measurement results in a steady-state phase shift due to the attenuation of the waveform. The phase shift can be correlated to the mass of antigens bound to the surface when the reaction reaches an equilibrium. Since the SH-SAW biosensor system is essentially a mass detection device, mass amplification strategies are necessary to achieve the desired fg $mL^{-1}$ to pg $mL^{-1}$ limits of detection when working with dilute samples. In one embodiment of the application, these biological mass amplifiers include engineered all-purpose endospores that express different epitopes and/or functional groups for bio-conjugation to whole immunoglobulins (IgG) or single-chain variable fragments (scFv). Engineered endospores have the advantage of displaying many binding sites, thereby increasing the rate of reaction. The all-purpose endospore for signal amplification is coated with an antibody-binding molecule (protein A for intact antibodies, protein L for either intact antibodies or scFv antibody fragments). ScFv's is utilized to improve the orientation of the binding site and/or enhance the binding affinity to the antigen, both of which result in an increase of the rate of reaction.

In another embodiment of this application, functionalized magnetic beads expressing scFv antibodies on the surface can be utilized to function as a mass amplification technique.

The rapid analysis of dilute samples in a fg $mL^{-1}$ to pg $mL^{-1}$ range can be challenging for even the most sensitive techniques. This is because at the very low concentration levels, there is typically a diffusional limit that restricts the rate of antigen binding. To overcome the diffusional limit, the biosensor is used in a convective-enhanced delivery modality where the sample is introduced to the surface of the sensor to overcome any diffusional limit imposed by having a dilute solution. To further enhance the signal-to-noise ratio and establish a quantitative measurement, the proposed biosensor employs a multi-reservoir system to sequentially deliver biological mass amplifiers and dilute detergent solutions thereby reducing non-specific binding and associated false positives (see FIGS. 14A-14C). When the biological mass amplifier is introduced after the analyte, the binding ratio of amplifier-to-analyte is unity, thus making the measurement quantitative.

In summary, consider the design constraints and solutions realized in the microfluidic system 10 of the illustrated embodiment of the invention as described above. The constraints imposed on the design of the microfluidic chamber 14 arise from the process of the biological conjugation between the analyte 20 and the antibody 22 located on the surface of the SAW detector 12. The microfluidic chamber 14 must address the unavoidable limitations of the limit of detection of the SAW detector (LOD) and the magnitude of the diffusion coefficient. The minimum threshold mass detected by a SAW detector 12 is not less than 1 picogram. The sensitivity of the SAW detector 12 must be set as the minimal threshold above the total SNR of the microfluidic system 10 taking into consideration the total surface area of the sensing lane 16, the density of the antibody 22 located on the sensing lane 16, and the total volume of the buffer 24 of 100 microliters. The design of the microfluidic system 10 is subject to the magnitude of the diffusion coefficient of the sample 18, and subject to the fact that natural conjugation between the analyte 20 and antibody 22 requires many hours to meet the minimum threshold mass of detection in the SAW detector 12. To obtain a signal to reliably represent the actual concentration of the analyte 20 in question, a design of a microfluidic chamber 14 is needed to address the limitation of low concentration of the analyte 20, the density of the antibody 22 on the sensing lane 16 of the SAW detector 12, and the diffusion coefficient limitation.

To overcome these unavoidable constraints the design of the microfluidic system 10 mixes analyte 20, such as any collected endospores or other mass amplifiers, and buffer 24 within a reservoir chamber 26, and generates a homogenous gross mixture 28. In one embodiment the endospore bearing analyte 20 and the buffer 24 are pre-loaded into the reservoir chamber 26 through a syringe 31 and sealing membrane 30, providing a foolproof loading protocol for handheld, field-portal, and disposable device. Since the typical diffusion coefficients would normally entail time domain which do not lend to the intended use of the invention as the device is meant to act as a handheld field-portable device providing near real time analytical results compared to conventional sensing techniques such as ELISA, PCR, and existing SAW techniques. The design of microfluidic system 10 uses a recirculating manifold 32 to enable the analyte 20 in a 100-microliter sample 18 to be sufficiently exposed to the antibodies 22 functionalized on sensing lane 16. In general, the analyte 20 must be positioned within 1 micrometer of the antibody 22 before capture or hybridization is possible. Recirculation of sample 18 increases the probability of the analyte 20 to fall within the hybridization range of the antibody 22 on the surface of the sensing lane 16, thereby overcoming the limitation of the diffusion coefficient. Unidirectional flow within the microfluidic chamber 14 is ensured by the use of check valve geometry or a nozzle-diffuser combination 34. A piezo pump 36 provides a convection enhanced delivery of mixture 28 to provide for uniform and controlled flow across the entire microfluidic chamber 14 based on duty-cycle and amplitude of the applied voltage (the duty-cycle is tailored to the association rate K+ and K−). The microfluidic chamber 14 incorporates a bubble trap 38 to maximize surface contact with a hydrophobic membrane 40 to release air within the mixture 28. Passive mixer 42 upstream from the SAW detector 12 enables a fine mixing of the mixture 28. A splitter-combiner 44 between the passive mixer 42 and SAW detector 12 provides for balanced distribution of mixture 28 into each of multiple lanes or channels 74 in SAW detector 12.

In the illustrated embodiment, the handheld device and portable detector used in the field is characterized by:

A time constraint of no more than 10-15 min to obtain results which are statistically commensurable with industry standards.

A diffusion coefficient as well as capture rate (K+/K−) are constants that cannot be altered, but by the use of convection enhanced delivery through recirculation technique provided by the manifold and its propellant mechanism, the increase of kinetics of the analyte within the buffer solution is increased, thereby reducing the time domain by increasing the probability of encounter of an analyte element with the antibody at the sensing lane of the SAW.

A mass enhancement technique is demonstrated experimentally by using gold nanoparticles, PHIX viruses, endospores, and or magnetic beads which reduces the limit of detection to the order of picogram to femtogram $mL^{-1}$ volume.

The method is demonstrates the ability of a multichambered fluidic apparatus to eliminate the need for an operator to perform multiple biochemistry steps such as mixing, conjugating, or cleaning (by use of a detergent) to remove unnecessary sedimentation of nonspecific binding particles, thereby reducing false positive results.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments include other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus, if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub combination or variation of a sub combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. A system for detecting an analyte in a small volume biological sample, the system comprising:
   a shear horizontal surface acoustic wave (SAW) detector with a sensing lane functionalized with an antibody;
   CED means for convection enhanced delivery (CED) of the sample to the SAW detector, the CED means comprising a distributing manifold and an active mixer coupled to the distributing manifold for uniformly distributing the mixture to increase kinetics of the analyte within a buffer solution for actively recirculating the biological sample through the system for a predetermined number of cycles in a predetermined time period to reduce time required for detection by increasing the probability of encounter of the analyte with the antibody in the sensing lane of a SAW detector;
   a SAW interface circuit; and
   a microcontroller,
   where the SAW interface circuit comprises a clock oscillator, an RF synthesizer coupled to the clock oscillator, a low pass filter and splitter having an input coupled to the RF synthesizer and an output coupled to the SAW detector, a phase/gain detector coupled to the low pass filter and the splitter and having a data input coupled to the SAW detector, an analog-to-digital converter having an input coupled to an output of the phase/gain detector and having an output coupled to the microcontroller, a pump driver, and a motor with a motor driver for mechanically loading a microfluidic cartridge.

2. The system according to claim 1, wherein the distributing manifold comprises:
   a plurality of channels associated with the SAW detector; and
   a closed microfluidic circuit in communication with the SAW detector,
   wherein the closed microfluidic circuit further comprises the active mixer coupled to a microfluidic reservoir chamber for mixing the analyte and buffer into a homogeneous mixture.

3. The system of claims 2, further comprising a pump chamber into which the analyte is transmitted from the microfluidic reservoir chamber.

4. The system of claim 2, wherein the closed microfluidic circuit comprises in sequence:
   the microfluidic reservoir chamber for mixing the analyte and the buffer;
   means for delivering a biological mass amplifier to modify the mass of the analyte detectable in a sensing channel to meet a limit of detection (LOD) of the SAW detector with a predetermined size of the sample; and/or means for delivering a detergent solution to retain quantitative capability of biosensor measurement and minimize non-specific binding.

5. The system of claim 1, where the distributing manifold and active mixer coupled to the distributing manifold for actively recirculating the biological sample through the system for a predetermined number of cycles in a predetermined time period to reduce time required for detection by increasing the probability of encounter of the analyte with the antibody in the sensing lane of a SAW detector is configured for detecting the analyte in the small volume sample of biological sample, when the small volume sample comprises 100 or less molecules of the analyte.

6. The system of claim 1, where the distributing manifold and active mixer coupled to the distributing manifold for actively recirculating the biological sample through the system for a predetermined number of cycles in a predetermined time period to reduce time required for detection by increasing the probability of encounter of the analyte with the antibody in the sensing lane of a SAW detector is configured for detecting the analyte in the small volume sample of biological sample, when the small volume sample comprises 10 or less molecules of the analyte.

7. The system of claim 1, where the distributing manifold and active mixer coupled to the distributing manifold for actively recirculating the biological sample through the system for a predetermined number of cycles in a predetermined time period to reduce time required for detection by increasing the probability of encounter of the analyte with the antibody in the sensing lane of a SAW detector is configured for detecting the analyte in the small volume sample of biological sample, when the small volume sample comprises one molecule of the analyte.

8. The system of claim 1 where the distributing manifold and active mixer coupled to the distributing manifold for actively recirculating the biological sample through the system for a predetermined number of cycles in a predetermined time period to reduce time required for detection by increasing the probability of encounter of the analyte with the antibody in the sensing lane of a SAW detector render the limit of detection (LOD) of the SAW detector at 1 picogram of analyte.

9. The system of claims 1, where the biological sample comprises a virus, Ab-Conjugated or scFv-conjugated endospore specifically attached to the analyte through an ELISA chain.

10. The system of claim 2, where the closed microfluidic circuit recirculates the mixed analyte and buffer through the closed microfluidic circuit a multiplicity of times within a predetermined time period less than or equal to one hour in duration.

11. The system of claim 2, where the closed microfluidic circuit recirculates the mixed analyte and buffer through the closed microfluidic circuit approximately 60 times within an approximately 5 minute duration.

12. The system of claim 4, where the analyte and the buffer are combined in the microfluidic reservoir chamber using a sample size of the order of 50 μL in an amount of buffer of the order of 100 μL.

13. The system of claim 1 further comprising a processor for processing a signal from the analyte, where the processor is comprised of a reader, and where the SAW interface circuit, the microcontroller for controlling the SAW detector through the SAW interface circuit, and a user interface associated with the microcontroller are disposed in the reader.

14. A system for detecting an analyte in a small volume biological sample, the system comprising:
- a shear horizontal surface acoustic wave (SAW) detector with a sensing lane functionalized with an antibody; and
- CED means for convection enhanced delivery (CED) of the sample to the SAW detector, the CED means comprising a distributing manifold and an active mixer coupled to the distributing manifold upstream from the SAW detector for uniformly distributing the mixture to increase kinetics of the analyte within a buffer solution in the SAW detector and for-actively recirculating the biological sample through the SAW detector.

15. The system according to claim 14, wherein the distributing manifold comprises:
- a plurality of channels associated with the SAW detector; and
- a closed microfluidic circuit in communication with the SAW detector, wherein the closed microfluidic circuit further comprises the active mixer coupled to a microfluidic reservoir chamber for mixing the analyte and buffer into a homogeneous mixture.

16. The system of claim 14, where the distributing manifold and active mixer coupled to the distributing manifold actively recirculates the biological sample through the system for a predetermined number of cycles in a predetermined time period to reduce time required for detection by increasing the probability of encounter of the analyte with the antibody in the sensing lane of a SAW detector renders the limit of detection (LOD) of the SAW detector at 1 picogram of analyte, or is configured for detecting the analyte in the small volume sample of biological sample, when the small volume sample consists of a sample size selected from one molecule, 10 or less molecules, or 100 or less molecules of the analyte.

* * * * *